US008852632B2

(12) United States Patent
Pourkavoos et al.

(10) Patent No.: US 8,852,632 B2
(45) Date of Patent: Oct. 7, 2014

(54) PHARMACEUTICAL FORMULATION CONTAINING A RELEASE RATE CONTROLLING COMPOSITION

(75) Inventors: Nazaneen Pourkavoos, Ambler, PA (US); James R. Ney, Lansdale, PA (US); Maria T. Cruanes, Lansdale, PA (US); Yunhui Wu, North Wales, NJ (US); Saurabh A. Palkar, Audubon, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 787 days.

(21) Appl. No.: 11/792,118

(22) PCT Filed: Dec. 2, 2005

(86) PCT No.: PCT/US2005/043727
§ 371 (c)(1),
(2), (4) Date: May 31, 2007

(87) PCT Pub. No.: WO2006/060711
PCT Pub. Date: Jun. 8, 2006

(65) Prior Publication Data
US 2007/0292504 A1    Dec. 20, 2007

Related U.S. Application Data

(60) Provisional application No. 60/632,944, filed on Dec. 3, 2004.

(51) Int. Cl.
*A61K 9/20* (2006.01)
*A61K 31/513* (2006.01)
*A61K 31/517* (2006.01)

(52) U.S. Cl.
CPC ............ *A61K 9/2054* (2013.01); *A61K 31/513* (2013.01); *A61K 9/2031* (2013.01); *A61K 31/517* (2013.01)
USPC ...................................... 424/464

(58) Field of Classification Search
None
See application file for complete search history.

(56) References Cited

U.S. PATENT DOCUMENTS

| 6,399,100 B1* | 6/2002 | Clancy et al. ............. 424/468 |
| 7,169,780 B2 | 1/2007 | Crescenzi et al. |
| 7,217,713 B2 | 5/2007 | Crescenzi et al. |
| 2003/0021840 A1* | 1/2003 | Infeld et al. ............. 424/452 |
| 2003/0175341 A1* | 9/2003 | Rampal et al. ............. 424/468 |
| 2005/0075356 A1 | 4/2005 | Di Francesco et al. |
| 2006/0046985 A1 | 3/2006 | Crescenzi et al. |
| 2006/0122205 A1 | 6/2006 | Belyk et al. |
| 2008/0118559 A1 | 5/2008 | Cruanes et al. |

FOREIGN PATENT DOCUMENTS

| WO | WO 03/035077 | * | 5/2003 | ........... A61K 31/515 |
| WO | WO 03/035077 A1 | | 5/2003 | |
| WO | WO 03/086319 A2 | | 10/2003 | |
| WO | WO 2004/058756 A1 | | 7/2004 | |
| WO | WO 2005/065656 A2 | | 7/2005 | |
| WO | WO 2006/060681 A2 | | 6/2006 | |
| WO | WO 2006/060731 A2 | | 6/2006 | |

OTHER PUBLICATIONS

Yang et al., "Controlled Release from Ordered Microstructures Formed by Poloxamer Block Copolymers," in "Controlled Drug Delivery," Published by American Chemical Society, 2000, pp. 364-374.*
Cao et al., "Formulation, release characteristics and bioavailability of novel monolithic hydroxypropylmethylcellulose matrix tablets containing acetaminophen," J. Cont. Release, 108, 2005, pp. 351-361.*
Saravanan et al., "The Effect of Tablet Formulation and Hardness on in Vitro Release of Cephalexin from Eudragit L100 Based Extended Release Tablets," Biol. Pharm. Bull., 25(4), 2002, pp. 541-545.*
Dow, "Using METHOCEL Cellulose Ethers for Controlled Release of Drugs in Hydrophilic Matrix Systems," 2000, pp. 1-36.*
Kibbe, A. et al. "Hydroxypropyl Methylcellulose", Handbook of Pharmaceutical Excipients, 2000, American Pharmaceutical Association, Washington, DC, pp. 252-255.
Kibbe, A. et al. "Poloxamer", Handbook of Pharmaceutical Excipients, 2000, American Pharmaceutical Association, Washington, DC, pp. 386-388.
Gustafsson et al. "Characterisation of particle properties and compaction behaviour of hydroxypropyl methylcellulose with different degrees of methoxy/hydroxypropyl substitution", European Journal of Pharmaceutical Sciences, 1999, vol. 9, pp. 171-184.
Hussain, et al. "A thermorheological investigation into the gelation and phase separation of hydroxypropyl methylcellulose aqueous systems", Polymer, 2002, vol. 43, pp. 5623-5628.
Malamataris et al. "Effect of particle size and sorbed moisture on the compression behaviour of some hydroxypropyl methylcellulose (HPMC) polymers", International Journal of Pharmaceutics, 1994, vol. 103, pp. 205-215.
Handbook of Pharmaceutical Additives, Second Edition, Synapse Information Resources, Inc., 2002, pp. 20 & 154.
Handbook of Pharmaceutical Excipients, Fifth Edition, The American Pharmaceutical Association and Pharmaceutical Press, 2006, pp. 132-135.
Handbook of Pharmaceutical Excipients, Second Edition, The American Pharmaceutical Association and Pharmaceutical Press, 1994, pp. 84-87.

(Continued)

*Primary Examiner* — Brian Gulledge
(74) *Attorney, Agent, or Firm* — Sheldon O. Heber; Jeffrey P. Bergman

(57) ABSTRACT

Pharmaceutical formulations suitable for oral administration in solid dosage forms are described. The compositions comprise an effective amount of a base salt of a compound of Formula (I) and a release rate controlling composition comprising a solubilizing agent, a gelling agent, and a water soluble filler; wherein $R^1$, $R^2$, $R^3$ and $R^4$ are defined herein. The formulations are suitable for use in the inhibition of HIV integrase, the treatment and prophylaxis of HIV infection, and the treatment, prophylaxis and delay in the onset of AIDS.

16 Claims, 4 Drawing Sheets

(56) References Cited

OTHER PUBLICATIONS

Avicel Product Selection Table, 2008, from FMC website—http://www.fmcbiopolymer.com/Pharmaceutical/-Products/Avicelforsoliddoseforms.aspx.

METHOCEL Premium Products for Pharmaceutical Applications from Dow Chemical Co. website—http://www.dow.com/dowexcipients/products/methocel.htm, 2008.

METHOCEL Cellulose Ethers-Technical Handbook, Dow Chemical Co., 2002.

* cited by examiner

PHARMACEUTICAL FORMULATION CONTAINING A RELEASE RATE CONTROLLING COMPOSITION

This application is the National Stage of International Application No. PCT/US2005/043727, filed on Dec. 2, 2005, which claims the benefit of U.S. Provisional Application No. 60/632,944, filed Dec. 3, 2004, the disclosure of which is incorporated by reference herein in its entirety.

FIELD OF THE INVENTION

The present invention is directed to pharmaceutical formulations suitable for oral administration in solid dosage forms comprising an effective amount of a salt of a drug product and a release rate controlling composition. More particularly, the drug product salt is a base salt of a hydroxypyrimidinone carboxamide and the release rate controlling composition comprises a solubilizing agent, a gelling agent, and a water soluble filler.

BACKGROUND OF THE INVENTION

The hydroxypyrimidinone carboxamides disclosed in WO03/035077 and the hydroxy-tetrahydropyridopyrimidinone carboxamides and related carboxamides disclosed in WO 2004/058756 are HIV integrase inhibitors useful for the treatment of HIV infection and AIDS. Certain of these carboxamide compounds exhibit relatively low aqueous solubility which can lead to poor absorption of the compound in the gastrointestinal (GI) tract following oral administration. The solubility of these compounds can be improved by administering the drugs in the form of base salts (i.e., the salts formed by reaction of the compounds with basic salts such as metal hydroxides), but the solubility of some of the resulting salts can change as a function of pH. More particularly, the base salts can be comparatively soluble in neutral or basic aqueous media, but can convert to less soluble forms under acidic conditions. Representative of such salts is the potassium salt of Compound A:

Compound A

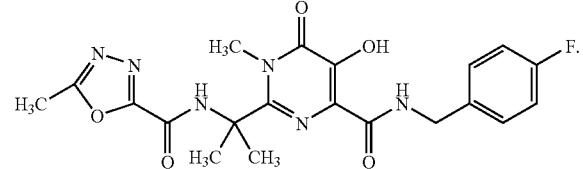

The potassium salt of Compound A is relatively soluble in neutral and basic aqueous solutions, but in acidic solutions it tends to disproportionate to the relatively insoluble free base form. When the Compound A K salt is administered orally in a solid dosage form, the compound can exhibit poor absorption into the systemic circulation due to the lost or significantly reduced solubility of the salt in the acidic conditions typically encountered in the stomach.

Satisfactory oral bioavailability can be achieved by formulating these salts with an antinucleating agent. For example, compressed tablet formulations of the Compound A K salt containing hydroxypropylmethylcellulose (e.g., HPMC 2910) as the antinucleating agent have exhibited improved solubility in in vitro dissolution tests and improved pharmacokinetics (PK) in animal studies compared to analogous formulations not containing the antinucleating agent. Orally administered tablet formulations of the Compound A K salt with HPMC have also afforded satisfactory pharmacokinetics (PK) in humans. It is believed that the antinucleating agent employed in these formulations can sufficiently inhibit and/or delay precipitation (or, stated another way, can provide prolonged supersaturation) of the drug compound under the acidic conditions of the stomach or the intestine, so as to permit the drug to be more efficiently absorbed into circulation.

On the other hand, the solid dosage formulations of the compound salts containing an antinucleating agent can have a relatively rapid absorption of the compound into the systemic circulation (i.e., a relatively short $T_{max}$=the postdose time to $C_{max}$, the maximum concentration of the compound in the plasma) and can be followed by a rapid decline. For example, the compressed tablet HPMC-containing formulations of Compound A K salt noted in the preceding paragraph have exhibited relatively high $C_{max}$ values, short $T_{max}$ values (e.g., from about 30 to 90 minutes) and relatively low plasma concentrations thereafter. High peak to trough plasma concentration ratios can be associated with adverse events, and low plasma concentrations subsequent to $T_{max}$ can result in little to no absorption of the drug outside the stomach and prior to elimination of the drug from the gastrointestinal tract (i.e., little or no absorption in the small intestine or colon). Accordingly, there exists a need for oral solid dosage formulations of these compounds which can control the release of the compound in a manner that provides an altered PK profile (i.e., a longer $T_{max}$, a lower peak to trough plasma concentration ratio, and/or higher minimum plasma concentrations following $T_{max}$) relative to that achieved by the antinucleating agent-based solid dosage formulations.

SUMMARY OF THE INVENTION

The present invention is directed to pharmaceutical formulations for oral administration comprising a hydroxypyrimidinone carboxamide or related fused ring carboxamides and a composition that controls the release of the carboxamide into the systemic circulation following administration. More particularly, the present invention includes a pharmaceutical formulation for oral administration as a solid dose, which comprises an effective amount of a base salt of a compound of Formula I (alternatively and more simply referred to herein as "Compound I") and a release rate controlling composition comprising a solubilizing agent, a gelling agent, and optionally a water soluble filler; wherein Formula I is:

(I)

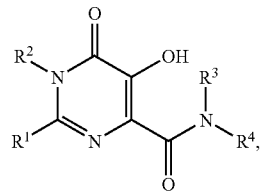

wherein $R^1$ is $C_{1-6}$ alkyl substituted with:
  (1) $N(R^A)$—C(=O)—$N(R^C)R^D$,
  (2) $N(R^A)$—C(=O)—$C_{1-6}$ alkylene-$N(R^C)R^D$,
  (3) $N(R^A)SO_2R^B$,
  (4) $N(R^A)SO_2N(R^C)R^D$,
  (5) $N(R^A)$—C(=O)—$C_{1-6}$ alkylene-$SO_2R^B$,
  (6) $N(R^A)$—C(=O)—$C_{1-6}$ alkylene-$SO_2N(R^C)R^D$, (7) $N(R^A)C(=O)C(=O)N(R^C)R^D$,
(8) $N(R^A)$—$C(=O)$-HetA,
(9) $N(R^A)C(=O)C(=O)$-HetA, or
(10) HetB;

$R^2$ is —$C_{1-6}$ alkyl;

or alternatively $R^1$ and $R^2$ are linked together such that the compound of Formula I is a compound of Formula II:

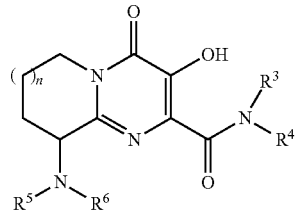

(II)

$R^3$ is —H or —$C_{1-6}$ alkyl;
$R^4$ is $C_{1-6}$ alkyl substituted with an aryl (e.g., phenyl), which is optionally substituted with from 1 to 4 substituents each of which is independently halogen, —OH, —$C_{1-4}$ alkyl, —$C_{1-4}$ alkyl-$OR^A$, —$C_{1-4}$ haloalkyl, —O—$C_{1-4}$ alkyl, —O—$C_{1-4}$ haloalkyl, —CN, —$NO_2$, —$N(R^A)R^B$, —$C_{1-4}$ alkyl-$N(R^A)R^B$, —$C(=O)N(R^A)R^B$, —$C(=O)R^A$, —$CO_2R^A$, —$C_{1-4}$ alkyl-$CO_2R^A$, —$OCO_2R^A$, —$SR^A$, —$S(=O)R^A$, —$SO_2R^A$, —$N(R^A)SO_2R^B$, —$SO_2N(R^A)R^B$, —$N(R^A)C(=O)R^B$, —$N(R^A)CO_2R^B$, —$C_{1-4}$ alkyl-$N(R^A)CO_2R^B$, methylenedioxy attached to two adjacent ring carbon atoms, phenyl, or —$C_{1-4}$ alkyl-phenyl;

$R^5$ is:
(1) $N(R^A)$—$C(=O)$—$N(R^C)R^D$,
(2) $N(R^A)$—$C(=O)$—$C_{1-6}$ alkylene-$N(R^C)R^D$,
(3) $N(R^A)SO_2R^B$,
(4) $N(R^A)SO_2N(R^C)R^D$,
(5) $N(R^A)$—$C(=O)$—$C_{1-6}$ alkylene-$SO_2R^B$,
(6) $N(R^A)$—$C(=O)$—$C_{1-6}$ alkylene-$SO_2N(R^C)R^D$,
(7) $N(R^A)C(=O)C(=O)N(R^C)R^D$,
(8) $N(R^A)$—$C(=O)$-HetA, or
(9) $N(R^A)C(=O)C(=O)$-HetA;

$R^6$ is —H or —$C_{1-6}$ alkyl;
n is an integer equal to 1 or 2;
each $R^A$ is independently —H or —$C_{1-6}$ alkyl;
each $R^B$ is independently —H or —$C_{1-6}$ alkyl;
$R^C$ and $R^D$ are each independently —H or —$C_{1-6}$ alkyl, or together with the nitrogen to which they are attached form a saturated 5- or 6-membered heterocyclic ring optionally containing a heteroatom in addition to the nitrogen attached to $R^C$ and $R^D$ selected from N, O, and S, where the S is optionally oxidized to S(O) or $S(O)_2$, and wherein the saturated heterocyclic ring is optionally substituted with 1 or 2 $C_{1-6}$ alkyl groups;

HetA is a 5- or 6-membered heteroaromatic ring containing from 1 to 4 heteroatoms independently selected from N, O and S, wherein the heteroaromatic ring is optionally substituted with 1 or 2 substituents each of which is independently —$C_{1-14}$ alkyl, —$C_{1-4}$ haloalkyl, —O—$C_{1-4}$ alkyl, —O—$C_{1-4}$ haloalkyl, or —$CO_2R^A$; and HetB is a 5- to 7-membered saturated heterocyclic ring containing from 1 to 4 heteroatoms independently selected from N, O and S, wherein each S is optionally oxidized to S(O) or $S(O)_2$, and the heterocyclic ring is optionally substituted with from 1 to 3 substituents each of which is independently halogen, —$C_{1-4}$ alkyl, —$C_{1-4}$ fluoroalkyl, —C(O)—$C_{1-4}$ alkyl, or —$C_{1-4}$ alkyl substituted with OH.

An embodiment of the present invention is the above-defined pharmaceutical formulation wherein in Compound I, $R^2$ is methyl; $R^3$ is —H; and $R^4$ is $CH_2$-phenyl wherein the phenyl is optionally substituted with 1 or 2 substituents each of which is independently bromo, chloro, fluoro, $CH_3$, $CF_3$, $C(O)NH_2$, $C(O)NH(CH_3)$, $C(O)N(CH_3)_2$, $SCH_3$, $SO_2CH_3$, or $SO_2N(CH_3)_2$; and all other variables are as defined above. In a feature of this aspect, $R^4$ is 4-fluorobenzyl, 3,4-dichlorobenzyl, 3-chloro-4-fluorobenzyl, or 4-fluoro-3-methylbenzyl. In another feature of this aspect, $R^4$ is 4-fluorobenzyl.

Pharmaceutical formulations of the present invention can provide an altered PK profile for Compound I compared to other orally administered solid dosage formulations. For example, a pharmaceutical formulation of the present invention containing a potassium salt of Compound A has exhibited a longer $T_{max}$, a lower peak to trough plasma concentration ratio, and higher minimum plasma concentrations following $T_{max}$ following oral administration compared to similar formulations employing an antinucleating agent instead of a release rate controlling composition. Without wishing to be bound by any particular theory, it is believed that the release rate controlling composition is responsible for the altered PK profile as follows: The solubilizing agent acts to prevent or minimize precipitation of Compound I (which, as noted above, can have low solubility particularly under the acidic conditions encountered in the stomach) in the GI tract by maintaining it in a solubilized form for several hours following administration. The gelling agent acts by forming a gel around particles of Compound I wherein the gel acts as a diffusion barrier that slows down release of Compound I for absorption into the systemic circulation. The water soluble filler dissolves relatively quickly following administration and acts to draw water into the gel layer formed by the gelling agent and thereby promote drug diffusion and release. The two components (or three components when the release rate controlling composition includes a water soluble filler) are employed in a manner and in amounts that act to maintain the active compound in solution and to prolong the release rate of the compound such that a safe and efficacious amount of the drug is absorbed into the systemic circulation over an extended period of time and from both the stomach and the intestinal tract.

The present invention also includes methods for preparing encapsulated and tabletted forms of pharmaceutical formulations of the invention. The present invention further includes use of a pharmaceutical formulation of the invention for the inhibition of HIV integrase, for the treatment or prophylaxis of HIV infection, or for the treatment, delay in the onset, or prophylaxis of AIDS.

Various embodiments, aspects and features of the present invention are either further described in or will be apparent from the ensuing description, examples and appended claims.

DETAILED DESCRIPTION OF THE INVENTION

Figure 1:
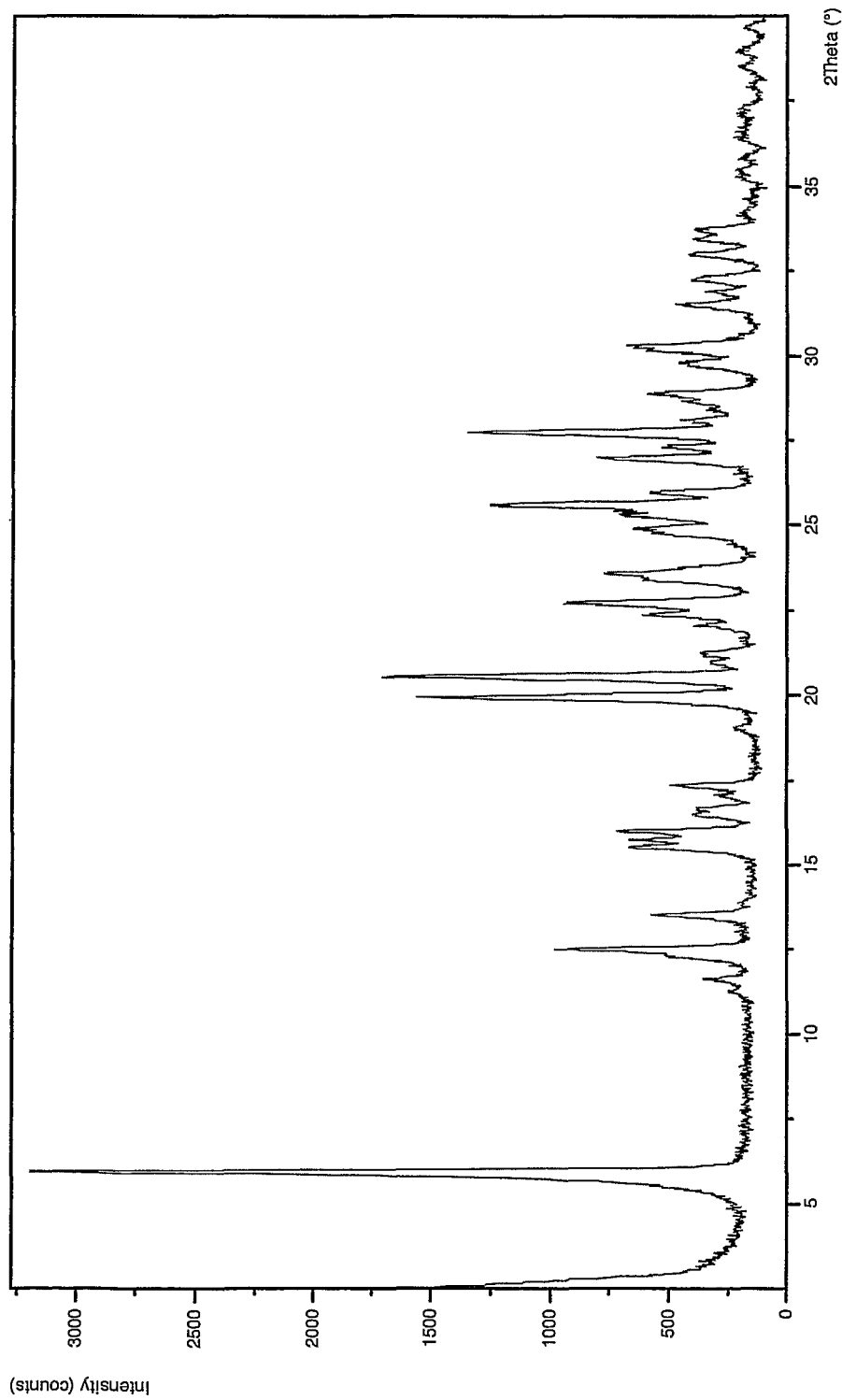
FIG. 1 is the X-ray powder diffraction pattern for the potassium salt of Compound A as prepared in Example 2.

The solid-dose, orally administered pharmaceutical formulations of the present invention include an effective amount of a base salt of a compound of Formula I. The compounds of Formula I are HIV integrase inhibitors. More particularly, representative compounds embraced by Formula I have been tested in an integrase inhibition assay in which strand transfer is catalyzed by recombinant integrase, and have been found to be active inhibitors of HIV integrase. Integrase inhibition activity can be determined, for example, using the assay described in Hazuda et al., *J. Virol.* 1997, 71: 7005-7011. Representative compounds have also been found to be active in an assay for the inhibition of acute HIV infection of T-lymphoid cells conducted in accordance with Vacca et al., *Proc. Natl. Acad. Sci. USA* 1994, 91: 4096-4100. Further description of representative compounds embraced by Formula I, methods for their preparation, and assays for measuring their integrase inhibition activity and their inhibition of HIV replication can be found in WO 03/035077, the disclosure of which is herein incorporated by reference in its entirety.

As used herein, the term "formulation" is intended to encompass an orally administered, solid dosage product comprising the specified ingredients, as well as any product which results, directly or indirectly, from combining the specified ingredients.

The term "effective amount" as used herein means that amount of Compound I (or another pharmaceutical agent) that elicits the biological or medicinal response in a tissue, system, animal or human that is being sought by a researcher, veterinarian, medical doctor or other clinician. The effective amount can be a "therapeutically effective amount" for the alleviation of the symptoms of the disease or condition being treated. The effective amount can also be a "prophylactically effective amount" for prophylaxis of the symptoms of the disease or condition being prevented. The term also refers to the amount of a compound of Formula I sufficient to inhibit HIV integrase and thereby elicit the response being sought (i.e., an "inhibition effective amount").

It is understood that the base salt of Compound I employed in pharmaceutical formulations embraced by the present invention is a pharmaceutically acceptable salt. The term "pharmaceutically acceptable salt" refers herein to a base salt which possesses the effectiveness of the parent compound and which is not biologically or otherwise undesirable (e.g., is neither toxic nor otherwise deleterious to the recipient thereof). Suitable salts include salts formed by reaction of Compound I with a base, including, for example, alkali metal salts (e.g., sodium or potassium salts), alkaline earth metal salts (e.g., calcium or magnesium salts) and ammonium salts. Alkali metal salts of the compounds can be formed by treating the compound dissolved in a suitable solvent with an aqueous solution of the alkali metal hydroxide (e.g., NaOH or KOH).

An embodiment of the present invention is the pharmaceutical formulation as originally defined above (i.e., as originally set forth in the Summary of the Invention), wherein the base salt of Compound I is an alkali metal salt of Compound I (e.g., a Na or K salt of Compound I).

The pharmaceutical formulations of the present invention include a release rate controlling composition comprising a solubilizing agent, a gelling agent, and optionally a water soluble filler. Suitable solubilizing agents include poloxamers and fatty acid macrogolglycerides. Poloxamers are block copolymers of ethylene oxide and propylene oxide. Suitable poloxamers include, for example, those having an average molecular weight in a range of from about 1000 to about 20,000 and an oxyethylene content of from about 40 to about 90 wt. % Representative poloxamers suitable for use in the present invention include poloxamer 188, poloxamer 237, poloxamer 338, and poloxamer 407. A suitable fatty acid macrogolglyceride is stearoyl macrogolglyceride, such as GELUCIRE® 50/13 (available from Gattefosse, Paramus, N.J.) which is a mixture of mono-, di- and triglycerides and mono- and di-fatty acid esters of polyethylene glycol with a melting range of 46.0 to 51.0° C. and an BLB value of 13.

Suitable gelling agents include glycerol esters of fatty acids such as glyceryl behenate (e.g., Compritol® 888ATO which is glycery behenate; available from Gattefosse) and high-viscosity HPMCs. The term "high-viscosity" HPMCs refers to an HPMC that produces a 2 wt. % (i.e., weight of polymer/weight of water) aqueous solution having a viscosity of at least about 2900 centipoise (cps) at 20° C. (1 cps=1 mPa sec). The high-viscosity HPMC typically produces a 2 wt. % solution having a viscosity of at least about 3100 cps (e.g., from about 3100 to about 100,000 cps) at 20° C. Suitable high-viscosity HPMCs include those sold under the trademark METHOCEL® (Dow Chemical) (e.g., METHOCEL grades K4M, K15M, and K100M) and METOLOSE® (Shin-Etsu). The high-viscosity HPMCs can be used singly or in mixtures of two or more, wherein the polymer mixture produces a 2 wt. % solution with an average viscosity of at least about 2900 cps and typically at least about 3100 cps. The average viscosity of the polymer mixture typically differs from the viscosity of each component polymer.

Suitable water soluble fillers include sugars such as lactose, glucose, fructose, mannitol, and dextrose. Lactose and mannitol are particularly suitable. Lactose is a preferred water soluble filler.

Another embodiment of the present invention is the pharmaceutical formulation as originally defined, wherein the solubilizing agent comprises a poloxamer; the gelling agent comprises a high-viscosity hydroxypropylmethylcellulose; and the optional water soluble filler comprises lactose.

Another embodiment of the present invention is a pharmaceutical formulation as originally defined, wherein the base salt of Compound I is employed in an amount in a range of from about 5 to about 75 wt. % on a free phenol basis; the solubilizing agent comprises a poloxamer which is employed in an amount in a range of from about 5 to about 25 wt. %; the gelling agent comprises high-viscosity hydroxypropylmethylcellulose which is employed in an amount in a range of from about 2 to about 15 wt. %; and the optional water soluble filler comprises lactose which is employed in an amount in a range of from zero to about 15 wt. %.

Pharmaceutical formulations of the present invention can contain additional components, including diluents, lubricants, disintegrants, antioxidants, and the like. Accordingly, another embodiment of the present invention is a pharmaceutical formulation as originally defined or as defined in any of the preceding embodiments, wherein the formulation further comprises a diluent and a lubricant.

Another embodiment of the present invention is the pharmaceutical formulation as originally set forth above or as set forth in any one of the preceding embodiments, wherein the formulation is encapsulated or compressed into a tablet.

Still another embodiment of the present invention is the pharmaceutical formulation as originally defined above, wherein Compound I is Compound A. This formulation is alternatively referred to herein as "Formulation F1" or the "F1 formulation".

Still another embodiment of the present invention is the F1 formulation as just defined, wherein the base salt of Compound I is an alkali metal salt of Compound A.

Still another embodiment of the present invention is the F1 formulation as defined above, wherein the base salt of Compound I is a potassium salt of Compound A. In an aspect of this embodiment, the potassium salt of Compound A is Form 1 crystalline potassium salt of Compound A, wherein the Form 1 K salt is an anhydrous crystalline salt characterized by an X-ray powder diffraction pattern obtained using copper $K_\alpha$ radiation (i.e., the radiation source is a combination of Cu $K_{\alpha 1}$ and $K_{\alpha 2}$ radiation) which comprises 2Θ values (i.e., reflections at 2Θ values) in degrees of 5.9, 12.5, 20.0, 20.6 and 25.6.

Still another embodiment of the present invention is Formulation F1 as originally set forth above, wherein the solubilizing agent comprises a poloxamer; the gelling agent comprises a high-viscosity hydroxypropylmethylcellulose; and the optional water soluble filler comprises lactose. In an aspect of this embodiment, the base salt of Compound A is a potassium salt of Compound A which is employed in an amount in a range of from about 5 to about 75 wt. % on a free phenol basis; the poloxamer is employed in an amount in a range of from about 5 to about 25 wt. %; the high-viscosity hydroxypropylmethylcellulose is employed in an amount in a range of from about 2 to about 15 wt. %; and the lactose is employed in an amount in a range of from zero to about 15 wt. %. In a preferred aspect of this embodiment, the base salt of Compound A is a potassium salt of Compound A which is employed in an amount in a range of from about 25 to about 75 wt. % on a free phenol basis; the poloxamer is employed in an amount in a range of from about 10 to about 20 wt. %; the high-viscosity hydroxypropylmethylcellulose is employed in an amount in a range of from about 3 to about 9 wt. %; and the lactose is employed in an amount in a range of from about 3 to about 9 wt. %. In this embodiment and the foregoing aspects thereof, a preferred poloxamer is poloxamer 407 (especially poloxamer 407 milled to an average particle size in a range of from about 50 to about 150 microns, and preferably to an average particle size in a range of from about 50 to about 105 microns); the high-viscosity hydroxypropylmethylcellulose is HPMC K4M; and the lactose is lactose hydrous spray dried. In particular, the milled poloxamer has been found to give more uniform and homogeneous mixing with particles of Compound A K salt (especially Form 1 crystalline K salt). In the foregoing aspects of this embodiment, the potassium salt of Compound A is preferably Form 1 crystalline potassium salt of Compound A.

Still another embodiment of the present invention is the F1 formulation as originally defined above or as defined in any of the preceding embodiments thereof, wherein the F1 formulation further comprises a diluent and a lubricant.

Still another embodiment of the present invention is the F1 formulation as originally defined above or as defined in any one of the preceding embodiments thereof, wherein the formulation is encapsulated or compressed into a tablet. In an aspect of this embodiment, Formulation F1 is encapsulated to provide a capsule containing the Compound A base salt (e.g., a Compound A K salt) in an amount in a range of from about 5 mg to about 1000 mg (e.g., from about 5 mg to about 900 mg, or from about 5 mg to about 600 mg, or from about 10 mg to about 400 mg). In another aspect of this embodiment, Formulation F1 is compressed into a tablet containing the Compound A base salt (e.g., a Compound A K salt) in an amount in a range of from about 5 mg to about 1000 mg (e.g., from about 5 mg to about 900 mg, or from about 5 mg to about 600 mg, or from about 10 mg to about 400 mg).

It is noted that any reference herein to an amount of a base salt of Compound I means the amount of Compound I in its free, non-salt form. Thus, for example, a tablet composition containing Compound I base salt in an amount in a range of from about 5 mg to about 1000 mg means a tablet composition containing an amount of the drug salt equivalent to about 5 mg to about 1000 mg of the Compound I parent (free phenol).

Still another embodiment of the present invention is a pharmaceutical formulation for oral administration as a solid dose (alternatively referred to herein as "Formulation F2" of the "F2 formulation"), which comprises (i) an effective amount of a potassium salt of Compound A, (ii) a release rate controlling composition comprising a solubilizing agent, a gelling agent, and a water soluble filler, (iii) a diluent, and (iv) a lubricant; wherein the solubilizing agent comprises a poloxamer; the gelling agent comprises a high-viscosity hydroxypropylmethylcellulose; the water soluble filler comprises lactose; the diluent comprises microcrystalline cellulose and optionally calcium phosphate; and the lubricant comprises a metal stearate and a metal stearyl fumarate. In an aspect of this embodiment, the potassium salt of Compound A is employed in an amount in a range of from about 40 to about 60 wt. % on a free phenol basis; the poloxamer is employed in an amount in a range of from about 10 to about 20 wt. %; the high-viscosity hydroxypropylmethylcellulose is employed in an amount in a range of from about 3 to about 9 wt. %; the lactose is employed in an amount in a range of from 3 to about 9 wt. %; the microcrystalline cellulose is employed in an amount in a range of from about 5 to about 30 wt. %; the calcium phosphate is employed in an amount in a range of from about zero to about 15 wt. %; and the metal stearate and metal stearyl fumarate are each independently employed in an amount in a range of from about 1 to about 3 wt. %. In a feature of the preceding aspect, the poloxamer is poloxamer 407 milled to an average particle size in a range of from about 50 to 150 microns; the high-viscosity hydroxypropylmethylcellulose is HPMC K4M; the lactose is lactose hydrous spray dried; the microcrystalline cellulose is AVICEL PH-102; the calcium phosphate is dibasic calcium phosphate; the metal stearate is magnesium stearate; and the metal stearyl fumarate is sodium stearyl fumarate. In this embodiment and its foregoing aspects, the potassium salt of Compound A is preferably Form 1 crystalline potassium salt of Compound A.

Another embodiment of the present invention is the F2 formulation as just defined or as defined in an aspect of feature thereof, wherein the formulation is encapsulated or compressed into a tablet, such as a capsule or tablet containing the potassium salt of Compound A on a free phenol basis in an amount in a range of from about 100 mg to about 600 mg.

Unless otherwise indicated, weight percents herein are based on the total weight of all the components in the composition (keeping in mind that, as noted earlier, the weight percent of the base salt of Compound I is expressed as the weight percent of the free base form of the compound).

As disclosed above, pharmaceutical formulations of the present invention can include a diluent and a lubricant. A diluent (also referred to in the art as a "filler") is a substance used to impart bulk to the composition. A diluent can be employed, for example, to provide sufficient bulk and/or compactibility to permit the composition to be compressed into a tablet having a practical size. Suitable diluents include anhydrous dibasic calcium phosphate, dibasic calcium phosphate dihydrate, tribasic calcium phosphate, calcium sulfate, carboxymethylcellulose calcium, microcrystalline cellulose, and powdered cellulose. A preferred diluent for use in the F1 and F2 formulations is microcrystalline cellulose optionally in combination with a calcium phosphate.

Suitable forms of microcrystalline cellulose for use in pharmaceutical formulations of the invention include, but are not limited to, the materials sold as AVICEL PH-01, AVICEL PH-102, AVICEL PH-103, and AVICEL PH-105 (all of which are available from FMC Corporation), and mixtures thereof. Thus, for example, the microcrystalline cellulose employed in Formulations F1 and F2 can be AVICEL PH-102 or AVICEL PH-105 or a mixture thereof.

The lubricant can have one or more functions depending upon the dosage form of the composition. The lubricant can, for example, prevent adhesion of compressed tablets to the compression equipment, it can improve the flow of granules prepared via granulation of the composition prior to their compression or encapsulation, and/or it can improve the flow of an ungranulated powder in the filling of a capsule. Suitable lubricants include calcium stearate, glyceryl monostearate, glyceryl palmitostearate, hydrogenated castor oil, hydrogenated vegetable oil, light mineral oil, magnesium stearate, mineral oil, polyethylene glycol, stearic acid, talc, zinc stearate, and sodium stearyl fumarate. In an aspect of the invention, the lubricant employed in the formulation of the invention is magnesium stearate, Na stearyl fumarate, or a combination of the two. When the pharmaceutical formulation is Formulation F1 or F2, the lubricant is typically a combination magnesium stearate and Na stearyl fumarate.

The pharmaceutical formulation of the invention can also contain a disintegrant, which is a substance, or a mixture of substances, employed to facilitate breakup or disintegration of the formulation after administration. Suitable disintegrants include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, povidone, sodium alginate, sodium starch glycolate, and starch. The disintegrant employed in the pharmaceutical formulation of the invention can be a superdisintegrant, such as croscarmellose sodium, crospovidone, or sodium starch glycolate.

An antioxidant can be employed in the pharmaceutical formulation of the invention to prevent or minimize oxidative degradation of the active ingredient and/or other components of the pharmaceutical formulation. Suitable antioxidants include a tocopherol or an ester thereof, an alkyl gallate (e.g., propyl gallate), butylated hydroxyanisole (BHA), butylated hydroxytoluene (BHT), ascorbic acid, sodium ascorbate, citric acid, and sodium metabisulfite. Pharmaceutical formulations of the present invention can, for example, include BHA.

Pharmaceutical formulations of the present invention can be formulated into compressed tablets or capsules. Compressed tablets can be prepared via granulation, wherein the overall particle size of a formulation is increased through the permanent aggregation of smaller particles. Wet or dry granulation can be employed. Wet granulation can be accomplished, for example, by wetting a well-mixed blend of the dry ingredients (e.g., the Compound I salt, the release rate controlling composition, a diluent, optionally a disintegrant, and optionally an antioxidant) with sufficient solvent (e.g., water or water with an alcohol co-solvent) to moisten the dry blend such that particles in the blend tack to one another to form larger particles, and then sieving, comminuting, or otherwise manipulating the size of the particles. Once formed, the resulting wet granulate can then be dried and milled into suitably sized particles (i.e., granules), the granules blended with a lubricant, and the lubricated granules compressed into tablets.

For moisture-sensitive compositions, granulation can be accomplished either by wet granulating with a non-aqueous solvent or by dry granulation. Dry granulation can also be an attractive alternative to wet granulation when the composition is thermally sensitive and subject to degradation at the temperatures employed during the drying of the wet granules. Dry granulation can be accomplished, for example, by dry blending the Compound I salt, the release rate controlling composition, a first portion of a lubricant and optionally other ingredients (e.g., a diluent, or a diluent and a disintegrant), and then compressing the blended mixture into slugs or rolling the blended mixture into a compact. The slugs or compact can then be sized (e.g., by passing through a mesh screen or a comminuting mill) to afford the dry granules, which can then be blended with the remaining portion of the lubricant, and the lubricated granules compressed into tablets.

The compressed tablets can be sugar coated to mask any unpleasant taste or film coated to protect the tablet from atmospheric degradation. The coating must also not adversely affect release of the drug following oral administration. A suitable film coating suspension is Opadry II BP (available from Colorcon, West Point, Pa.), which is a partially hydrolyzed polyvinyl alcohol and macrogol/PEG 3350-based polymer. The films can be applied by spraying the suspension on the tablets and then drying. Film coating techniques suitable for use with the present invention are described in *Remington's Pharmaceutical Sciences*, $18^{th}$ edition, edited by A. R. Gennaro, 1990, Mack Publishing Co., pp. 1665-1675.

Encapsulated pharmaceutical formulations of the present invention can be formed, for example, by granulating the ingredients of the formulation (i.e., the Compound I base salt, the release rate controlling composition, and optionally one or more other ingredients such as a diluent and/or lubricant) via wet or dry granulation as described above, filling capsules (e.g., hard gelatin capsules) with a suitable amount of the granules, and sealing the capsules.

Technology and equipment suitable for preparing solid dosage forms of the pharmaceutical formulations of the present invention (e.g., capsules and compressed tablets) are described in *Remington's Pharmaceutical Sciences*, $18^{th}$ edition, edited by A. R. Gennaro, 1990, Chapter 89.

The present invention includes a process (alternatively referred to herein as "Process P1" or the "P1 process") for preparing a compressed tablet pharmaceutical formulation comprising an effective amount of a base salt of Compound I, a solubilizing agent, a gelling agent, optionally a water-soluble filler, a diluent, and a lubricant; wherein the method comprises:

(A) blending a mixture of the Compound I base salt, the solubilizing agent, the gelling agent, the optional water-soluble filler, the diluent, and a first portion of the lubricant;

(B) sieving the blended mixture, and then further blending the sieved mixture;

(C) rolling the sieved and blended mixture to form a compact, and then sizing the resulting compact to form granules;

(D) blending the granules with the remaining portion of the lubricant; and (E) compressing the lubricated granules of Step D to obtain the tablet.

Embodiments of the P1 process include the process as just described incorporating one or more of the features (i) to (xiv) as follows:

(i-a) the base salt of Compound I is an alkali metal salt of Compound I;

(i-b) the base salt of Compound I is a sodium salt or a potassium salt of Compound I;

(i-c) the base salt of Compound I is a base salt of Compound A;

(i-d) the base salt of Compound I is an alkali metal salt of Compound A;

(i-e) the base salt of Compound I is a potassium salt of Compound A; or (i-f) the base salt of Compound I is the Form 1 crystalline potassium salt of Compound A;

(ii-a) the base salt of Compound I (e.g., the K salt of Compound A) is employed in an amount in a range of from about 5 to about 75 wt. % on a free phenol basis; or (ii-b) the base salt of Compound I (e.g., the K salt of Compound A) is employed in an amount in a range of from about 25 to about 75 wt. % (or from about 40 to about 60 wt. %) on a free phenol basis; or (iii-a) the solubilizing agent comprises a poloxamer;

(iii-b) the solubilizing agent comprises poloxamer 407; or (iii-c) the solubilizing agent comprises poloxamer 407 milled to an average particle size in a range of from about 50 to about 150 microns (or in a range of from about 50 to about 105 microns);

(iv-a) the solubilizing agent comprises a poloxamer (e.g., poloxamer 407, optionally milled to an average particle size of from about 50 to about 150 microns) which is employed in an amount in a range of from about 5 to about 25 wt. %; or (iv-b) the solubilizing agent comprises a poloxamer (e.g., poloxamer 407, optionally milled to an average particle size of from about 50 to about 150 microns) which is employed in an amount in a range of from about 10 to about 20 wt. %;

(v-a) the gelling agent comprises a high-viscosity hydroxypropylmethylcellulose; or (v-b) the gelling agent comprises HPMC K4M (vi-a) the gelling agent comprises a high-viscosity hydroxypropylmethylcellulose (e.g., HPMC K4M) which is employed in an amount in a range of from about 2 to about 15 wt. % (or in a range of from about 3 to about 9 wt. %); or (vi-b) the gelling agent comprises a high-viscosity hydroxypropylmethylcellulose (e.g., HPMC K4M) which is employed in an amount in a range of from about 3 to about 9 wt. %);

(vii-a) the optional water soluble filler comprises lactose; or (vii-b) the optional water soluble filler comprises lactose hydrous spray dried;

(viii-a) the optional water soluble filler comprises lactose (e.g., lactose hydrous spray dried) which is employed in an amount in a range of from zero to about 15 wt. %; or (viii-b) the optional water soluble filler comprises lactose (e.g., lactose hydrous spray dried) which is employed in an amount in a range of from about 3 to about 9 wt. %;

(ix-a) the diluent comprises microcrystalline cellulose; or (ix-b) the diluent comprises AVICEL PH-102;

(x-a) the diluent comprises microcrystalline cellulose (e.g., AVICEL PH-102) which is employed in an amount in a range of from about 5 to about 50 wt. %; or (x-b) the diluent comprises microcrystalline cellulose (e.g., AVICEL PH-102) which is employed in an amount in a range of from about 5 to about 40 wt. %;

(xi-a) the lubricant comprises a metal stearate; or (xi-b) the lubricant comprises magnesium stearate;

(xii-a) the lubricant comprises a metal stearate (e.g., magnesium stearate) which is employed in an amount in a range of from about 0.5 to about 5 wt. %; or (xii-b) the lubricant comprises a metal stearate (e.g., magnesium stearate) which is employed in an amount in a range of from about 0.5 to about 3 wt. %;

(xiii-a) the process further comprises: (F) coating the compressed tablet; or (xiii-b) the process further comprises: (F) coating the compressed tablet with a film coating suspension (e.g., Opadry II HP) to afford a coated tablet in which the coating is from about 2 to about 4% of the weight of the compressed tablet; and (xiv-a) the base salt of Compound I (e.g., potassium salt of Compound A) is employed in a per tablet amount in a range of from about 100 mg to about 600 mg on a free phenol basis; or (xiv-b) the base salt of Compound I (e.g., potassium salt of Compound A) is employed in a per tablet amount of about 100 mg, 200 mg, 300 mg, 400 mg, 500 mg, or 600 mg on a free phenol basis.

The present invention also includes a compressed tablet pharmaceutical formulation prepared by the Process P1 as originally set forth above or as set forth in any of the foregoing embodiments of the P1 process.

The present invention includes a process (alternatively referred to herein as "Process P2" or the "P2 process") for preparing a compressed tablet pharmaceutical formulation comprising an effective amount of a potassium salt of Compound A, a solubilizing agent, a gelling agent, a water-soluble filler, a first diluent, a second diluent, a first lubricant and a second lubricant; wherein the method comprises:

(A) blending a mixture of the Compound A K salt, the solubilizing agent, the gelling agent, the water-soluble filler, the first diluent, second diluent, a first portion of the first lubricant, and the second lubricant;

(B) sieving the blended mixture, and then further blending the sieved mixture;

(C) rolling the sieved and blended mixture to form a compact, and then sizing the resulting compact to form granules;

(D) blending the granules with the remaining portion of the first lubricant; and (E) compressing the lubricated granules of Step D to obtain the tablet.

An embodiment of the P2 process is the P2 process as just described, wherein the solubilizing agent comprises a poloxamer; the gelling agent comprises a high-viscosity hydroxypropylmethylcellulose; the water soluble filler comprises lactose; the first diluent is microcrystalline cellulose; the second diluent is calcium phosphate; the first lubricant is a metal stearate; and the second lubricant is a metal stearyl fumarate.

Another embodiment of the P2 process is the P2 process as originally described, wherein the potassium salt of Compound A is employed in an amount in a range of from about 40 to about 60 wt. % on a free phenol basis; the solublizing agent is a poloxamer which is employed in an amount in a range of from about 10 to about 20 wt. %; the gelling agent is a high-viscosity hydroxypropylmethylcellulose which is employed in an amount in a range of from about 3 to about 9 wt. %; the water soluble filler is lactose which is employed in an amount in a range of from 3 to about 9 wt. %; the first diluent is microcrystalline cellulose which is employed in an amount in a range of from about 5 to about 25 wt. %; the second diluent is calcium phosphate which is employed in an amount in a range of from about 5 to about 25 wt. %; the first lubricant is a metal stearate which is employed in an amount in a range of from about 1 to about 3 wt. %; and the second lubricant is a metal stearyl fumarate which is employed in an amount in a range of from about 1 to about 3 wt. %

Still another embodiment of the P2 process is the P2 process as described in either of the foregoing embodiments thereof, wherein the poloxamer is poloxamer 407 milled to an average particle size in a range of from about 50 to 150 microns; the high-viscosity hydroxypropylmethylcellulose is HPMC K4M; the lactose is lactose hydrous spray dried; the microcrystalline cellulose is AVICEL PH 102; the calcium phosphate is dibasic calcium phosphate; the metal stearate is magnesium stearate; and the metal stearyl fumarate is sodium stearyl fumarate.

Still another embodiment of the P2 process is the P2 process as originally described or as described in any of the foregoing embodiments thereof, wherein the potassium salt of Compound A is Form 1 crystalline potassium salt of Compound A.

Still another embodiment of the P2 process is the P2 process as originally described or as described in any of the foregoing embodiments thereof, wherein the process further comprises: (F) coating the compressed tablet. In an aspect of this embodiment, the compressed tablet is coated with a film coating suspension (e.g., Opadry II HP) to afford a coated tablet in which the coating is from about 2 to about 4% of the weight of the compressed tablet.

Still another embodiment of the P2 process is the P2 process as originally described or as described in any of the foregoing embodiments thereof, wherein the potassium salt of Compound A is employed in a per tablet amount in a range of from about 100 mg to about 600 mg on a free phenol basis. In an aspect of this embodiment, the Compound A K salt is employed in a per tablet amount of about 100 mg, about 200 mg, about 300 mg, about 400 mg, about 500 mg, or about 600 mg.

The present invention also includes a compressed tablet pharmaceutical formulation prepared by the Process P2 as originally set forth above or as set forth in any of the foregoing embodiments of the P2 process.

The pharmaceutical formulations of the present invention are useful in the inhibition of HIV integrase, the treatment or prophylaxis of infection by HIV and the treatment, prophylaxis, or the delay in the onset of consequent pathological conditions such as AIDS. Treating AIDS, the prophylaxis of AIDS, delaying the onset of AIDS, treating HIV infection, or prophylaxis of HIV infection is defined as including, but not limited to, treatment or prophylaxis of a wide range of states of HIV infection: AIDS, ARC, both symptomatic and asymptomatic, and actual or potential exposure to HIV. For example, the compositions of this invention are useful in treating or prophylaxis of infection by HIV after suspected past exposure to HIV by such means as blood transfusion, exchange of body fluids, bites, accidental needle stick, or exposure to patient blood during surgery.

The present invention includes a method for inhibiting HIV integrase in a subject in need thereof which comprises administering to the subject the pharmaceutical formulation of the present invention as originally defined above. The invention also includes a method for treating or prophylaxis of HIV infection or for treating, prophylaxis, or delaying the onset of AIDS in a subject in need thereof, which comprises administering to the subject the pharmaceutical formulation of the invention as originally defined above. In these methods, the pharmaceutical formulation of the present invention can optionally be employed in combination with one or more anti-HIV agents selected from HIV antiviral agents, anti-infective agents, and immunomodulators. Embodiments of these methods include the methods as just described wherein the pharmaceutical formulation of the invention is a formulation as set forth in any one of the foregoing embodiments thereof (including, inter alia, the F1 formulation and the compressed tablet formulations resulting from the P1 and P2 processes) as set forth above.

The term "subject" (used interchangeably herein with "patient") refers to an animal, preferably a mammal, most preferably a human, who has been the object of treatment, observation or experiment.

When a pharmaceutical formulation of the present invention is employed or administered in combination with another agent (e.g., when the F1 formulation is administered in combination with an anti-HIV agent), the formulation and agent can be administered separately or together, and when administered separately, the formulation and agent can be given concurrently or at different times (e.g., alternately).

The present invention also includes a pharmaceutical formulation for oral administration as a solid dose, which comprises a base salt of a compound of Formula I and a release rate controlling composition as originally defined and described in the Summary of the Invention (i) for use in, (ii) for use as a medicament for, or (iii) for use in the preparation of a medicament for: (a) inhibiting HIV integrase, (b) treating or prophylaxis of infection by HIV, or (c) treating, prophylaxis of, or delaying the onset of AIDS. Embodiments of these uses include the uses as just described wherein the pharmaceutical formulation of the invention as originally defined is replaced with the above-described embodiments thereof (which include, inter alia, the F1 formulation and the compressed tablet formulations resulting from the P1 and P2 processes). In these uses, the pharmaceutical formulations of the present invention can optionally be employed in combination with one or more anti-HIV agents selected from HIV antiviral agents, anti-infective agents, and immunomodulators.

The term "anti-HIV agent" means an agent (other than a compound of Formula I) which is effective in one or more of the following uses: inhibiting integrase or another enzyme required for HIV replication or infection, prophylaxis of HIV infection, treating HIV infection, delaying the onset of AIDS, prophylaxis of AIDS, or treating AIDS.

Suitable HIV antiviral agents for use in combination with the pharmaceutical formulation of the invention include, for example, HIV protease inhibitors (e.g., indinavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). These agents can be used in their free form or in the form of pharmaceutically acceptable salts. These agents can also be used per se, but are typically incorporated into suitable pharmaceutical compositions.

The pharmaceutical formulations of this invention can be administered in a solid form suitable for oral administration. The compositions can, for example, be administered in the form of capsules or tablets. The compositions can be administered so as to provide the active ingredient in a dosage range of from about 0.001 to about 1000 mg/kg of mammal (e.g., human) body weight per day in a single dose or in divided doses. One preferred dosage range is from about 0.01 to about 500 mg/kg body weight per day in a single dose or in divided doses. Another preferred dosage range is from about 0.1 to about 100 mg/kg body weight per day in single or divided doses.

The pharmaceutical formulations of the invention can suitably be provided in the form of tablets or capsules for oral administration, wherein each tablet or capsule contains from about 1 to about 1000 milligrams of the active ingredient, particularly 1, 5, 10, 15, 20, 25, 50, 75, 100, 150, 200, 250, 300, 400, 500, 600, 700, 800, 900 and 1000 milligrams of the active ingredient for the symptomatic adjustment of the dosage to the patient to be treated. In particular, pharmaceutical formulations of the present invention containing a potassium salt of Compound A (e.g., Form 1) are preferably dosed to adult humans as capsules or tablets, wherein the dosage is 100 mg to 600 mg of Compound A twice per day.

The specific dose level and frequency of dosage for any particular patient will depend upon a variety of factors including the activity of the specific drug compound employed, the metabolic stability and length of action of that compound, the age, body weight, general health, sex, diet, mode and time of administration, rate of excretion, drug combination, the severity of the particular condition, and the host undergoing therapy. The appropriate dose level of a particular drug suitable for a particular patient can be determined by the person of ordinary skill in the art without undue experimentation.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (or alternatively "alkanediyl") having a number of carbon atoms in the specified range. Thus, for example, "—$C_{1-6}$ alkylene-" refers to any of the C1 to C6 linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "aryl" refers to (i) phenyl or (ii) a 9- or 10-membered bicyclic, fused carbocyclic ring system in which at least one ring is aromatic. Aryl is typically phenyl or naphthyl, and is more typically phenyl.

The term "HetA" refers to an optionally substituted a 5- or 6-membered heteroaromatic ring containing from 1 to 4 heteroatoms independently selected from N, O and S. In one embodiment, HetA is an optionally substituted heteroaromatic ring selected from the group consisting of pyridinyl, pyrrolyl, pyrazinyl, pyrimidinyl, pyridazinyl, triazinyl, furanyl, thienyl, imidazolyl, pyrazolyl, triazolyl, tetrazolyl, oxazolyl, isooxazolyl, thiazoly, isothiazolyl, and oxadiazolyl; wherein the optional substitution is with 1 or 2 substituents each of which is independently —$C_{1-4}$ alkyl, —$C_{1-4}$ haloalkyl, —O—$C_{1-4}$ alkyl, —O—$C_{1-14}$ haloalkyl, or —$CO_2$—$C_{1-4}$ alkyl. It is understood that HetA is attached to the rest of the compound of Formula I at any ring atom (i.e., any carbon atom or any heteroatom) provided that a stable compound results.

The term "HetB" refers to an optionally substituted a 5- to 7-membered saturated heterocyclic ring containing from 1 to 4 heteroatoms independently selected from N, O and S. In one embodiment, HetB is an optionally substituted saturated heterocyclic ring selected from the group consisting of pyrrolidinyl, imidazolidinyl, piperidinyl, piperazinyl, morpholinyl, thiomorpholinyl, thiazinanyl, and tetrahydropyranyl, wherein the optional substitution is with 1 or 2 substituents each of which is independently —$C_{1-4}$ alkyl, —$C_{1-4}$ haloalkyl, —$C(O)CF_3$, —$C(O)CH_3$, or —$CH_2CH_2OH$. It is understood that HetA can be attached to the rest of the compound of Formula I at any ring atom (i.e., any carbon atom or any heteroatom) provided that a stable compound results. In another embodiment, HetB is selected from the group consisting of

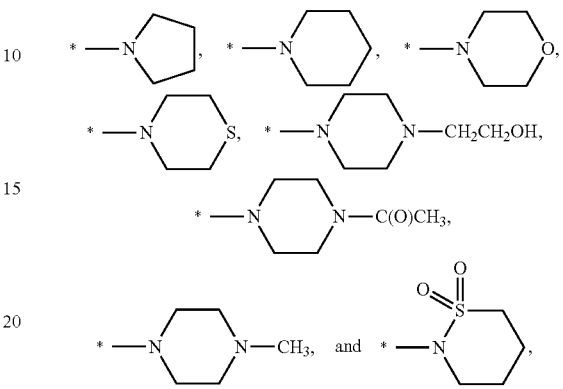

wherein * denotes the point of attachment to the rest of the molecule.

In the compound of Formula I, $R^C$ and $R^D$ together with the nitrogen to which they are attached can form a saturated 5- or 6-membered heterocyclic ring optionally containing a heteroatom in addition to the nitrogen attached to $R^C$ and $R^D$ selected from N, O, and S, where the S is optionally oxidized to S(O) or S(O)$_2$, and wherein the saturated heterocyclic ring is optionally substituted with 1 or 2 $C_{1-6}$ alkyl groups. In one embodiment, the saturated heterocyclic ring formed by $R^C$ and $R^D$ and the nitrogen to which they are attached is selected from the group consisting of 4-morpholinyl, 4-thiomorpholinyl, 1-piperidinyl, 1-piperazinyl optionally substituted with $C_{1-4}$ alkyl (e.g., methyl), and 1-pyrrolidinyl.

Unless expressly stated to the contrary, all ranges cited herein are inclusive. For example, a heterocyclic ring described as containing from "1 to 4 heteroatoms" means the ring can contain 1, 2, 3 or 4 heteroatoms. As another example, a pharmaceutical formulation comprising a base salt of Compound I in a range of from about 25 to about 75 wt. % means the composition can contain about 25 wt. % of Compound I, about 75 wt. % of Compound I, or any amount therebetween.

When any variable (e.g., $R^A$ and $R^B$) occurs more than one time in Formula I or in any other formula depicting and describing a compound whose salt can be employed in pharmaceutical formulations of the invention, its definition on each occurrence is independent of its definition at every other occurrence. Also, combinations of substituents and/or variables are permissible to the extent such combinations result in stable compounds.

A "stable" compound is a compound which can be prepared and isolated and whose structure and properties remain or can be caused to remain essentially unchanged for a period of time sufficient to allow use of the compound for the purposes described herein (e.g., use in the form of a salt in a pharmaceutical formulation of the invention).

As a result of the selection of substituents and substituent patterns, certain of the compounds of Formula I whose salts can be employed in the present invention can have asymmetric centers and can occur as mixtures of stereoisomers, or as individual diastereomers, or enantiomers. The salts of all isomeric forms of these compounds, whether individually or in mixtures, can be employed in pharmaceutical compositions of the present invention.

Compounds of Formula I can also exist as tautomers due to keto-enol tautomerism. The salts of all tautomers of the hydroxypyrimidinone compounds of Formula I, both singly and in mixtures, can be employed in pharmaceutical formulations of the present invention.

Abbreviations used herein include the following:
ACN=acetonitrile
AIDS=acquired immunodeficiency syndrome
APCI=atmospheric pressure chemical ionization
ARC=AIDS related complex
Cbz=benzyloxycarbonyl
DIEA=diisopropylethylamine
DMADC=dimethylacetylene dicarboxylate
DMF=N,N-dimethylformamide
DMSO=dimethylsulfoxide
DSC=differential scanning calorimetry
EDTA=ethylenediaminetetraacetic acid
EtOH=ethanol
Eq.=equivalent(s)
GI=gastrointestinal
HIV=human immunodeficiency virus
HPLC=high-performance liquid chromatography
HPMC=hydroxypropylmethylcellulose
IPA=isopropyl alcohol
KF=Karl Fisher titration for water
LC=liquid chromatography
LCAP=LC area percent
LCWP=LC weight percent
Me=methyl
MeOH=methanol
MRM=multiple reaction monitoring
MS=mass spectroscopy
MSA=methanesulfonic acid
MTBE=methyl tertiary butyl ether
MW=molecular weight
NMM=N-methylmorpholine
NMR=nuclear magnetic resonance
PK=pharmacokinetic(s)
SDS=sodium dodecyl sulfate
TG=thermogravimetric
THF=tetrahydrofuran
XRPD=x-ray powder diffraction The following examples serve only to illustrate the invention and its practice. The examples are not to be construed as limitations on the scope or spirit of the invention.

EXAMPLE 1

Preparation of Compound A and a Crystalline Potassium Salt Thereof

Step 1: Strecker Amine Formation

| Material | MW | Eq. | Moles | Mass | Volume | density (g/mL) |
|---|---|---|---|---|---|---|
| acetone cyanohydrin (a) | 85.1 | 1.0 | 129.3 | 11.0 kg | 11.8 L | 0.932 |
| MTBE | | 4.0 | | | 44 L | |
| ammonia (g) | 17.03 | 1.5 | 193.9 | 3.30 kg | 4.9 L | 0.674 |

Acetone cyanohydrin (11.5 kg, 12.3 L) was charged to a 5-gallon autoclave and the vessel placed under 5 psi nitrogen pressure. The autoclave was cooled to 10° C., and ammonia gas (~3.44 kg), pressurized to 30 psi, was fed into the vessel until the reaction reached complete conversion as determined by GC assay (less than 0.5% a). The resulting suspension was transferred to a polyjug and the autoclave rinsed with MTBE (approximately 17 L). The reaction mixture and rinse were then charged to a 100-L extractor followed by MTBE (15 L), the mixture agitated, and the layers carefully separated. The aqueous layer was back-extracted with MTBE (5 L) and the layers carefully separated. The organic layers were combined and charged to a 100 L flask, equipped with a batch concentrator, through an in-line filter, and the batch was concentrated (15-20° C., low vacuum) to about 20 L to remove any excess ammonia. The aminonitrile was obtained in 97% assay yield (11.1 kg) by NMR as a solution in MTBE.

Step 2: Addition of Benzyloxycarbonyl (CBz) Protective Group

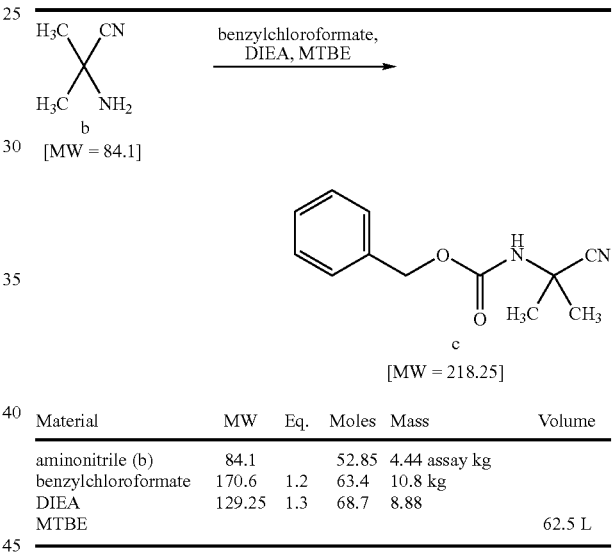

| Material | MW | Eq. | Moles | Mass | Volume |
|---|---|---|---|---|---|
| aminonitrile (b) | 84.1 | | 52.85 | 4.44 assay kg | |
| benzylchloroformate | 170.6 | 1.2 | 63.4 | 10.8 kg | |
| DIEA | 129.25 | 1.3 | 68.7 | 8.88 | |
| MTBE | | | | | 62.5 L |

To a visually clean 100-L flask containing a 5-L addition funnel, thermocouple and nitrogen inlet was charged a 59 wt. % solution of cyanoamine b in MTBE (4.44 assay kg). The solution was further diluted with MTBE (62.5 L) to bring the concentration to approximately 15 mL/g. Benzylchloroformate (1.20 equiv, 10.42 kg, 61.10 mol) was then charged in over 15 minutes via the addition funnel at such a rate as to maintain the batch temperature below 35° C. DIEA (1.3 equiv, 8.88 kg, 68.70 mol) was then added over 1.5 hours to the yellow slurry while maintaining the batch temperature below 35° C. The slurry became slightly more soluble as DIEA was added but two phases were observed when stirring was stopped. The reaction mixture was aged for 16 hours at 20-25° C., after which DI water (20 L, 4.5 mL/g) was charged into the batch. The batch was then transferred to a 100-L extractor and the phases were separated. The organic layer was then washed with 3×10 L of water and then 15 L of brine. The organic layer was transferred via a 10 µm inline filter to a 100 L round bottom flask and subsequently solvent switched to 90:10 heptane:MTBE. Crystallization occurred during the solvent switch and the resulting white crystalline product was filtered and washed with 3×5 L of 90:10 heptane:MTBE. A total of 10.1 kg of product (88% yield) was obtained in greater than 99 HPLC A %. A total of 26.7 kg of product was obtained in 3 batches with an average isolated yield of 86%.

Step 3: Amidoxime Formation

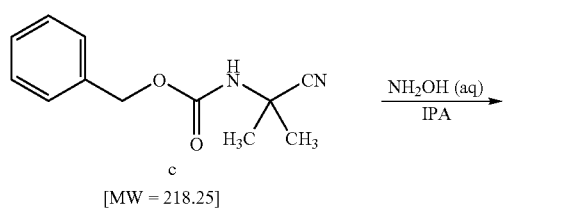 [SMILES: CC(C)(C#N)NC(=O)OCc1ccccc1]

| Material | MW | Eq. | Mass | Volume |
|---|---|---|---|---|
| protected aminonitrile (c) | 218.25 | 1 | 15 g | |
| NH$_2$OH (50 wt. % in water) | | 1.2 | | 5.05 mL |

| Material | MW | Eq. | Mass | Volume |
|---|---|---|---|---|
| IPA | | | | 40 mL + 10 mL |
| n-heptane | | | | 40 mL + 50 mL |

A solution of aminonitrile (15 g) in IPA (40 mL) was warmed to 60° C. with stirring and NH$_2$OH in water (5.05 mL) was added at this temperature over the course of 20 minutes. The clear mixture was then aged at 60° C. for 3 hours, wherein product began to crystallize out of solution at this temperature after 2 hours. The slurry was then cooled to 0°-5° C. and n-heptane (40 mL) was added dropwise over 20 minutes. After stirring for 2 hours at 0°-5° C., the slurry was filtered and the cake was washed with a 20% IPA in heptane solution (60 mL), and then dried under vacuum with a nitrogen stream at room temperature to give pure amide oxime in 88% yield.

Step 4: Formation of Hydroxypyrimidinone

| Material | MW | Eq. | Mass | Volume | Density (g/mL) |
|---|---|---|---|---|---|
| amidoxime (d) | 251.28 | 1 | 2.9 kg | | |
| DMADC | 142.11 | 1.08 | 1.77 | | 1.16 |
| MeOH | | | | 12 L + 6 L | |
| xylenes | | | | 15 L | |
| MTBE | | | | 9 L | |

To a slurry of amidoxime (2.90 kg) in methanol (12 L) was added dimethyl acetylenedicarboxylate (1.77 kg) over 20 minutes. A slow exotherm ensued such that the temperature of the slurry increased from 20° C. to 30° C. over 15-20 minutes. After 1.5 hours, HPLC indicated greater than 95% conversion to the intermediate cis/trans adducts. The solvent was then switched to xylenes under reduced pressure (maximum temperature=50° C.), wherein 2 volumes [2×7.5 L] were added and reduced to a final volume of 7.5 L. The reaction mixture was then heated to 90° C. and kept at this temperature for 2 hours, while flushing the remaining MeOH out with a nitrogen sweep. The temperature was then increased in 10° C. increments over 3.5 hours to 125° C. and held at this temperature for 2 hours. The temperature was then finally increased to 135° C. for 5 hours. The reaction mixture was then cooled to 60° C. and MeOH (2.5 L) was added. After 30 minutes MTBE (9 L) was added slowly to build a seed bed. The batch was then cooled to 0° C. for 14 hours, and then further cooled to −5° C. and aged 1 hour before filtration. The solids were displacement washed with 10% MeOH/MTBE (6 L then 4 L; prechilled to 0° C.) and dried on the filter pot under a nitrogen sweep to afford 2.17 kg (51.7% corrected yield; 99.5 wt %).

HPLC method: Column: Zorbax C-8 4.6 mm×250 mm; 40% ACN/60% 0.1% $H_3PO_4$ to 90% ACN/10% 0.1% $H_3PO_4$ over 12 minutes, hold 3 minutes then back to 40% ACN over 1 minute. Retention times: amidoxime d—2.4 minutes, DMAD—6.7 minutes, intermediate adducts—8.4 and 8.6 minutes (8.4 minute peak cyclizes faster), product e—5.26 minutes, xylenes—several peaks around 10.4-10.7 minutes.

Step 5: N-Methylation

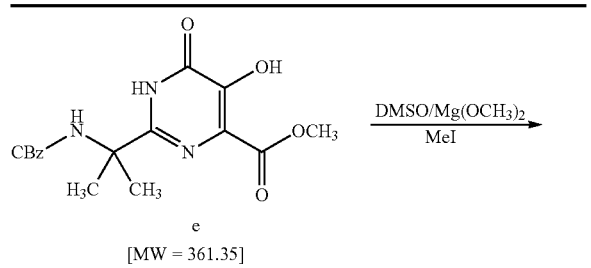

e
[MW = 361.35]

f
[MW = 375.38]

| Material | MW | Eq. | Mass | Volume |
|---|---|---|---|---|
| pyrimidine diol (e) | 361.35 | 1 | 2 kg | |
| Mg(OMe)$_2$, 8 wt.% in MeOH | | 2 | 11.95 kg | 13.4 L |
| MeI | | 4 | 3.14 kg | 1.38 L |
| DMSO | | | | 16 L |
| 2M HCl | | | | 20 L |
| MeOH | | | | 14 L |
| Na bisulfite 5 wt.% in water | | | | 2 L |
| water | | | | 60 L |

To a solution of the pyrimidine diol e (2 kg) in DMSO (16 L) was added a solution of Mg(OMe)$_2$ in MeOH (11.95 kg), after which excess MeOH was evaporated under vacuum (30 mm Hg) at 40° C. for 30 minutes. The mixture was then cooled down to 20° C., after which MeI (1.38 L) was added and the mixture stirred at 20-25° C. for 2 hours, and then at 60° C. for 5 hours under pressure in a closed flask. HPLC showed that the reaction was complete. The mixture was then cooled to 20° C., after which MeOH (14 L) was added, followed by the slow addition of 2 M HCl (20 L) [exotherm] over 60 minutes. Sodium bisulfite (5 wt. %, 2 L) was then added to quench excess I2, with the solution turning white. Water (40 L) was then added over 40 minutes and the slurry stirred for 40 minutes in an ice bath, and then filtered. The filter cake was washed first with water (20 L) and then with MTBE:MeOH 9/1 (30 L) to remove O-methylated by-product. HPLC showed less than 0.5 A % O-methylated product after washing. The solid was dried overnight at room temperature under vacuum with an N2 stream to give 1.49 kg of N-methylpyrimidone (70% yield, corrected for purity of starting material and product).

Step 6: Amine Coupling

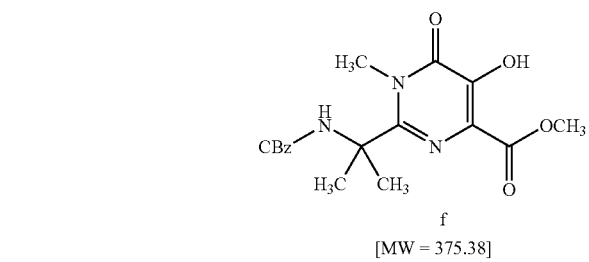

f
[MW = 375.38]

g
[MW = 468.48]

| Material | MW | Eq. | Mass | Volume |
|---|---|---|---|---|
| N-methylpyrimidinone (f) | 375.38 | 1 | 1.4 kg | |
| 4-fluorobenzylamine | 125.15 | 2.2 | 1.05 kg | |
| EtOH | | | | 14 L |
| water | | | | 14 L |
| acetic acid | | | | 0.55 L |

To a slurry of N-methylated pyrimidinone f (1.4 kg) in EtOH (14 L) at 4° C. was slowly added 4-fluorobenzylamine (1.05 kg) over 15 minutes, wherein an exotherm to 9° C. was observed during addition of the first 1 mole equivalent of the amine. The slurry became very thick and vigorous stirring was required. The reaction was warmed to 72° C. over 2 hours and maintained at this temperature for 1 hour and 45 minutes. The solution became extremely viscous at 45° C. where a small exotherm was observed to 50° C., after which the slurry slowly freed up and became homogeneous after 1 hour at 72° C. An HPLC sample assay (HPLC method was similar to that employed in Step 4 above) at the end of the reaction showed less than 0.5 A % N-methylated pyrimidinone. The reaction was then cooled to 60° C. and acetic acid (0.55 L) was added over 30 minutes, followed by the addition of water (6.7 L) over 30 min and then the addition of seed (3.0 g) to initiate crystallization. After 30 min at 60° C., more water (7.3 L) was added over 30 minutes and the reaction mixture allowed to cool to ambient temperature overnight. After 13 hours, the temperature was at 20° C., at which point the reaction mixture was filtered and the slurry washed with 50% water/EtOH (2×4 L). The solids were dried on the filter pot under vacuum/N2 flow to a constant weight to afford a white solid product (1.59 kg; 90% corrected yield; 99% LCWP and 99.7% LCAP as determined by HPLC method similar to that employed in Step 4 above).

Step 7: Hydrogenation of Cbz-amide

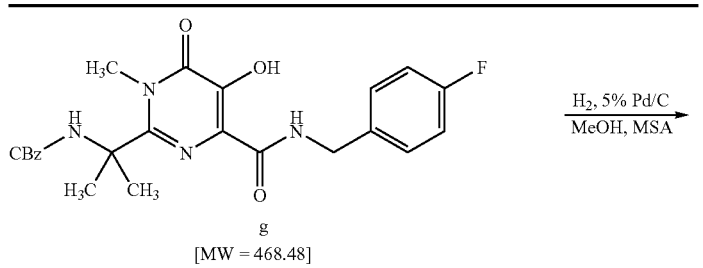

g
[MW = 468.48]

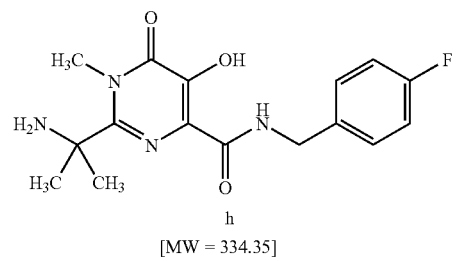 [SMILES: Cn1c(C(C)(C)N)nc(C(=O)NCc2ccc(F)cc2)c(O)c1=O]

h
[MW = 334.35]

| Material | MW | mmoles | Mass | Volume |
|---|---|---|---|---|
| CBz amide (g) | 468.48 | 21.33 | 10 g | |
| MeOH | | | | 80 mL |
| 5% Pd/C (50% wet) | | | 0.15 g | |
| MSA | 96.1 | 22.4 | | 1.45 mL |
| water | | | | 8 mL |
| cake wash (4:1 MeOH:H$_2$O) | | | | 20 mL |
| 1 N NaOH | | 22.4 | | 22.4 mL |
| final cake wash (water) | | | | 30 mL |

A stainless steel hydrogenation vessel was preconditioned with MeOH, Pd/C catalyst and MSA under the reaction conditions described below. Cbz-amide g (10 g) was then slurried in MeOH (80 mL) in the preconditioned vessel. MSA (1.45 mL) was added to the slurry in one portion at room temperature. 5% Pd/C (0.15 g, 50% wet) was also added to the hydrogenation vessel. Hydrogen was charged to the vessel in three successive vacuum/hydrogen purge cycles, after which the mixture was hydrogenated at 40 psig for 3-4 hour at 50° C. Following hydrogenation, water (8 mL) was added to the reaction mixture, the mixture was stirred, and the catalyst was filtered and washed with 4:1 MeOH:water (20 mL). The pH of combined filtrates was adjusted to pH 7 to 8.0 by slow addition of 1 N NaOH (22.4 mL), which precipitated a solid. The slurry was stirred at 0-5° C. for 4 hours and the solid filtered, washed with water (30 mL), collected and dried in vacuo at 50° C. The product amine (as hydrate) was obtained as a white crystalline solid (7.7 g) in 96% yield (corrected for KF), 89% LCWP, 99.8% LCAP, KF=11 wt. %.

HPLC Method A (product assay): column: 25 cm×4.6 mm Zorbax RX-C8; mobile phase: A=0.1% H$_3$PO$_4$, B=CH$_3$CN, O minutes (80% A/20% B), 20 minutes (20% A/80% B), 25 minutes (20% A/80% B); flow: 1.0 mL/minute; wavelength: 210 nm; column temperature: 40° C.; retention times: desfluoroamine byproduct—5.5 min, amine product—5.85 minutes, toluene—16.5 minutes, Cbz-amide—16.82 minutes.

HPLC Method B (product purity): column: 25 cm×4.6 mm YMC-basic; mobile phase: A=25 mmol KH$_2$PO$_4$ adjusted to pH=6.1, B=CH$_3$CN, O minutes (90% A/10% B), 30 minutes (30% A/70% B), 35 minutes (30% A/70% B); flow: 1 mL/minute; wavelength: 210 nm; column temperature: 30° C.; retention times: des-fluoroamine—9.1 minutes, amine—10.1 minutes, toluene—24.2 minutes, Cbz amide—25.7 minutes.

Step 8: Oxadiazole Coupling
Part A: Preparation of Oxadiazole K Salt

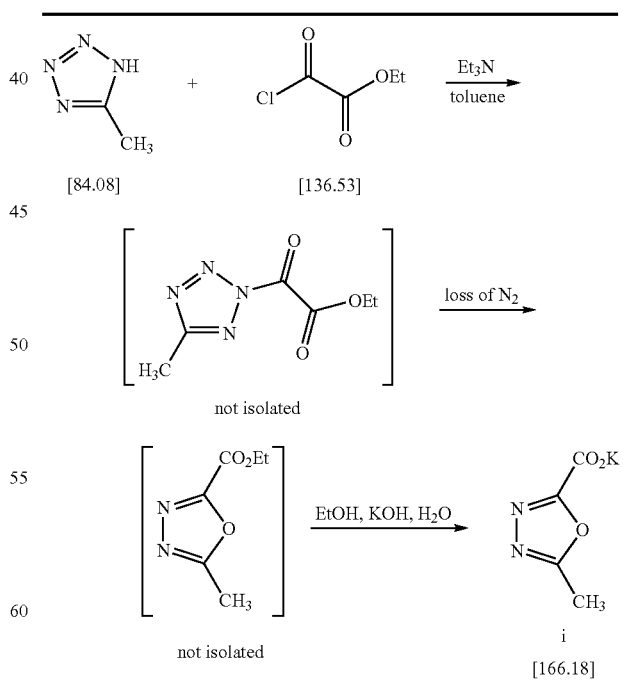

| Material | Eq. | Mole | Mass | Volume | Density |
|---|---|---|---|---|---|
| 5-methyltetrazole (96 wt. %) | 1.0 | 28.54 | 2.5 kg (2.4 kg) | | |

| | | | | | |
|---|---|---|---|---|---|
| ethyloxalyl chloride | 1.03 | 29.4 | 4.014 kg | 3.29 L | 1.22 |
| triethylamine | 1.05 | 29.97 | 3.033 kg | 4.21 L | 0.72 |
| toluene | | | | 74 L | |
| EtOH (punctilious) | | | | 61 L | |
| MTBE | | | | 15 L | | of 41 L). The ethanol solution was cooled to 10° C. and KOH aq. (8.0 L) was added over 30 minutes, and the resulting thick slurry was then stirred for 40 minutes at room temperature while the oxadiazole K salt crystallized out. The solid was filtered off, washed with 11 L of EtOH and finally with 15 L of MTBE. The solid was dried overnight under vacuum at 20° C. with a nitrogen stream to yield 4.48 kg (90.8%) of the K-salt i.

Part B: Oxadiazole Coupling

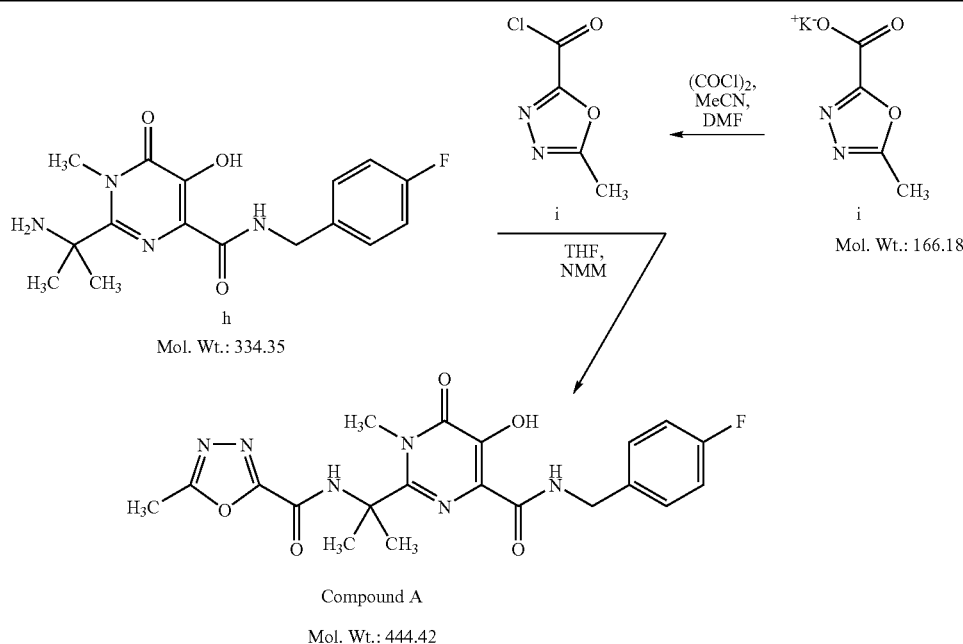

Compound A
Mol. Wt.: 444.42

| Reagent | Mass | mL | Moles | Eq. |
|---|---|---|---|---|
| oxadiazole K salt i | 33.8 g (96.1 wt %) | | 0.20 | 2.2 |
| ACN | | 280 mL | | |
| DMF | 0.33 | | | |
| oxalyl chloride | 23.7 g | 16.3 mL | 0.19 | 2.1 |
| free amine h | 30 g (99 wt %) | | 0.089 | 1 |
| THF | | 821 mL | | |
| NMM | 21.56 g | 23.4 mL | 0.21 | 2.4 |
| NH$_4$OH (30% in H$_2$O) | 62.3 g | 69 mL | 0.53 | 6 |
| HCl (2N) | | 500 mL | | |
| IPA | | 920 mL | | |
| water | | 400 mL | | |
| MeOH | | 300 mL | | |

-continued

| | |
|---|---|
| KOH aq. *20 wt. %) | 8 L |
| 10% brine | 5 L |

Ethyl oxalylchloride (4.01 kg) was slowly added to a mixture of 5-methyltetrazole (2.50 kg), triethylamine (3.03 kg) in toluene (32 L) at 0° C. at such a rate that the temperature stays below 5° C. The resulting slurry was stirred for 1 hour at 0-5° C. then the triethylamine/HCl salt was filtered off. The solid was washed with 27 L of cold toluene (5° C.). The combined filtrates were kept at 0° C. and were slowly added to a hot solution of toluene (50° C., 15 L) over 40-50 minutes (N$_2$ gas evolution), then the solution was aged at 60-65° C. for 1 hour. After cooling at 20° C., the toluene solution was washed with 5 L of 10% brine, then solvent switched to ethanol (reduced to 8 L, then 17 L of EtOH was added, then concentrated down to 8 L, then 33 liters of EtOH were added to adjust final volume A 500 mL round bottom flask was charged with oxadiazole K salt i (33.8 g) followed by ACN (280 mL) and DMF (0.33 mL) with strong stirring. The resulting slurry was then cooled down to 0-5° C. and oxalyl chloride (23.7 g) was added over the course of 20 minutes in order to maintain the internal temperature at less than 5° C. The resulting acyl chloride-containing slurry was then aged for 1 hour.

To a 2 L round bottom flask the free amine h (30 g) was added followed by THF (821 mL). The resulting slurry was cooled down to 0-5° C., after which NMM (21.56 g) was added and the slurry so obtained was stirred for 10 minutes at the cold temperature. The previously prepared acyl chloride-containing slurry was added slowly to the free amine slurry over the course of 20 minutes such that the temperature did not exceed 5° C. The slurry was then aged for 1.5 hours at 0-5° C. At this time HPLC showed no more amine h (<0.5% LCAP, 100% conversion). The reaction mixture was then quenched with NH$_4$OH (30% in water) (69 mL) which was added over the course of 3 minutes. The resulting yellow slurry was then stirred for an additional hour at temperatures less than 10° C. The yellow slurry was then acidified to pH 2-3 with HCl (2N) (500 mL). To the resulting red wine colored solution, IPA (920 mL) was added. The low boiling point organic solvents were then evaporated under reduced pressure (40 torr) at room temperature to a final solution volume of 1100 mL, at which volume crystalline Compound A began to precipitate. Water (400 mL) was then added to this new slurry over the course of 10 minutes, and the slurry aged overnight at room temperature. The aged slurry was filtered and the solid obtained was washed with water (170 mL), followed by a swish wash with cold MeOH (300 mL, previously cooled in an ice bath), and finally by a swish wash with water (700 mL). The solid so obtained was dried overnight under vacuum and nitrogen stream to give 35.5 g of Compound A (91% yield).
Step 9: Formation of a Crystalline Potassium Salt of Compound A Acetonitrile (50 mL) and anhydrous Compound A (5.8 g, 97.4 wt. %) were charged at room temperature to a jacketed 125 mL round bottom flask equipped with a mechanical stirrer and equipped with a nitrogen inlet (i.e., the crystallization was conducted under nitrogen). The resulting slurry was agitated at 45° C. until the solids were completely in solution. Form 1 crystalline Compound A K salt was then charged to the solution as seed (0.184 g, 3 wt % to theoretical K salt). Aqueous KOH 30% w/v solution (0.98 eq., 2.33 mL, 0.0125 moles) was then added with the following charge profile while maintaining batch at 45° C.:

0.466 mL over 5 hours, 0.0932 mL/hr (20 mol %)
1.864 mL over 7 hours, 0.2663 mL/hr (80 mol %)

The resulting slurry was cooled to 20° C. and aged at 20° C. until the concentration of Compound A in the mother liquor was measured to be less than 4 g/L. The batch was filtered, the cake washed with ACN (3×12 mL), and then dried under vacuum at 45° C., with a small nitrogen sweep, until the amount of ACN and water present as determined by thermogravimetric analysis was less than 1 wt. %. The K salt of Compound A was obtained in >99 A % by HPLC analysis.

EXAMPLE 2

Form 1 Crystalline Potassium Salt of Compound A

Part A: Preparation

Ethanol (147 mL), water (147 mL), and Compound A (97.9 g assay by HPLC) were charged to a 1 L round bottom flask equipped with mechanical stirrer, addition funnel, nitrogen inlet (i.e., run conducted under nitrogen), and a thermocouple. Aqueous KOH (45% w/w, 0.98 eq., 18.5 mL, 216 mmoles) was added to the suspension over 10 minutes at 21° C. The resulting suspension was agitated for 0.5 hour resulting in the dissolution of a majority of the solids, after which the batch was filtered through a 1 μm filter directly into a 5 L round bottom flask equipped with mechanical stirrer, addition funnel, nitrogen inlet, and thermocouple. The 1 L flask was rinsed with 1:1 (v/v) water/EtOH (48 mL) and the rinse was filtered into the 5 L crystallization vessel. The filtered solution was seeded with crystalline Form 1 Compound A K salt (200 mg) at room temperature and then aged for 1 hour to build a good seed bed, after which the suspension was diluted with EtOH (1.57 L) at 20° C. over 1.5 hour The batch was then cooled to about 4° C. and aged until the concentration of Compound A in the mother liquor was measured to be 4.7 g/L. The batch was filtered, the crystallization vessel rinsed with 50 mL EtOH into the filter, the cake washed with EtOH (4×100 mL), and then dried under vacuum and a nitrogen tent until the amount of EtOH present by NMR was about 0.4 mol % relative to the potassium salt. The potassium salt of Compound A was obtained in 88% yield (91.5 g assay by HPLC, 99 area % by HPLC analysis).

Part B: Characterization

An XRPD pattern of a K salt prepared in the manner described in Part A was generated on a Philips Analytical X'Pert Pro X-ray powder diffractometer using a continuous scan from 2.5 to 40 degrees 2 Θ over about 12 minutes (i.e., 0.02° step size with 40 seconds/step), 2 RPS stage rotation, and a gonio scan axis. Copper K-Alpha 1 ($K_{\alpha 1}$) and K-Alpha 2 ($K_{\alpha 2}$) radiation was used as the source. The experiment was run under ambient conditions. Characteristic 2Θ values in the XRPD pattern (shown in FIG. 1) and the corresponding d-spacings include the following:

| Peak No. | d-spacing (Å) | 2 Theta |
|---|---|---|
| 1 | 14.9 | 5.9 |
| 2 | 7.1 | 12.5 |
| 3 | 4.4 | 20.0 |
| 4 | 4.3 | 20.6 |
| 5 | 3.5 | 25.6 |

Figure 2:
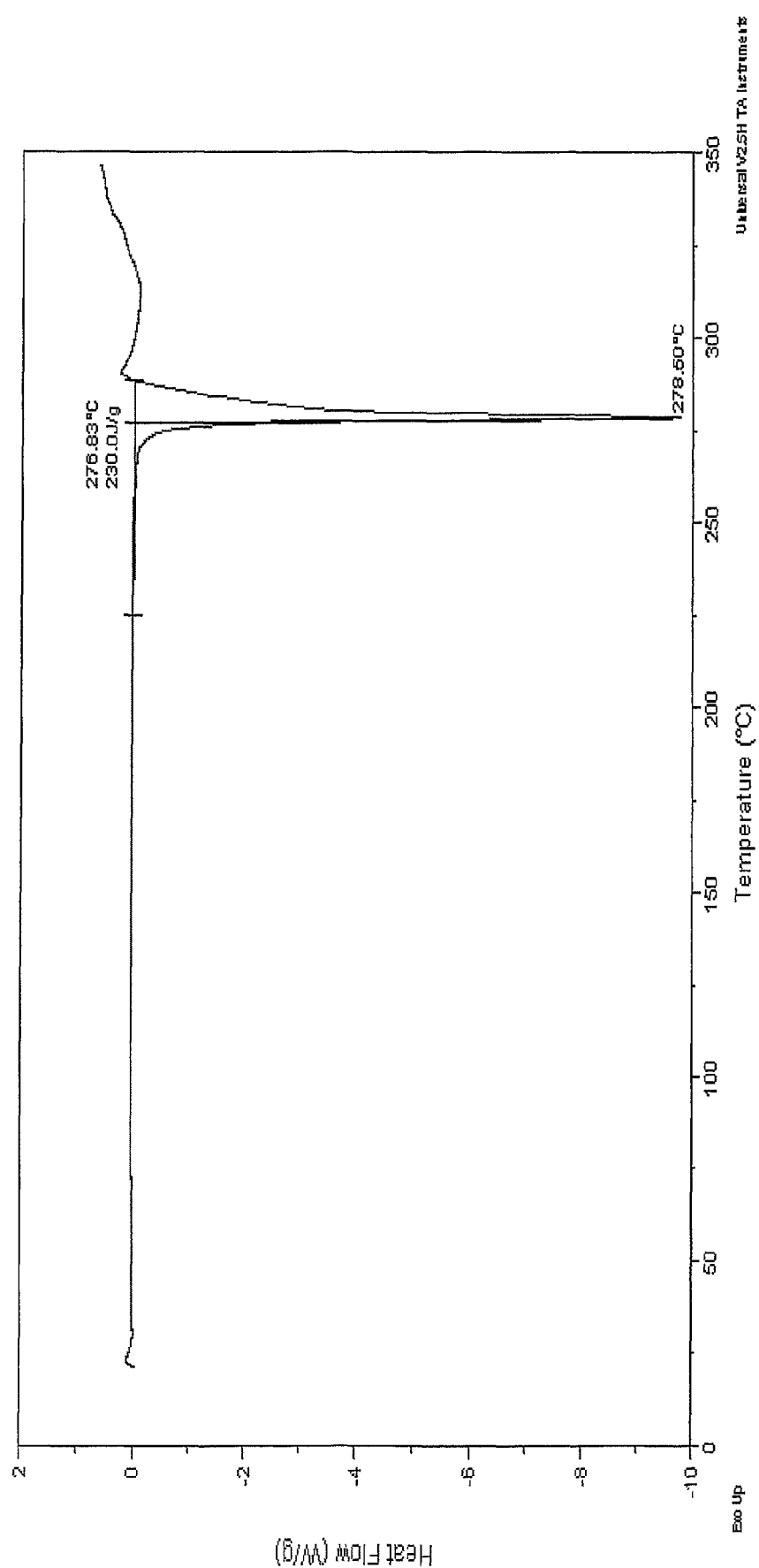
FIG. 2 is the DSC curve for the potassium salt of Compound A as prepared in Example 2.

A K salt prepared in the manner described in Part A was also analyzed by a TA Instruments DSC 2910 differential scanning calorimeter at a heating rate of 10° C./min from room temperature to 350° C. in a crimped pinhole aluminum pan in a nitrogen atmosphere. The DSC curve (shown in FIG. 2) exhibited a single, sharp endotherm with a peak temperature of about 279° C. and an associated heat of fusion of about 230.0 J/gm. The endotherm is believed to be due to melting.

A thermogravimetric analysis was performed with a Perkin-Elmer Model TGA 7 under nitrogen at a heating rate of 10° C./min from room temperature to about 350° C. The TG curve showed a 0.3% weight loss during heating to 250° C.

Hygroscopicity data was obtained on a VTI Symmetrical Vapor Sorption Analyzer Model SGA-1. Data was collected at room temperature from 5-95% relative humidity and back, 5% relative humidity change per step. Equilibrium conditions were 0.01 weight percent change in 5 minutes with a maximum equilibration time of 180 minutes. The data indicated that the material had a 1.8% weight increase when equilibrated at 95% RH at 25° C. When equilibrated back down to 5% RH, the material returned back to approximately its dry weight. An XRPD analysis of the material after the hygroscopicity experiment showed that the material had not changed phases.

K salt prepared as described in Part A was also assayed by HCl titration using a Brinkmann Metrohm 716 DMS Titrino. The assay results indicated the salt was a monopotassium salt.

EXAMPLE 3

Preparation of Compressed Tablets Containing Compound a Potassium Salt

| Ingredient | Amount per Tablet (mg) | Amt per batch (wt. percent) |
|---|---|---|
| Compound A K salt[1] | 434.4 | 50.0 |
| (on free phenol basis) | (400) | (46.0) |
| microcrystalline cellulose (AVICEL PH102) | 112.9 | 13.0 |

-continued

| Ingredient | Amount per Tablet (mg) | Amt per batch (wt. percent) |
|---|---|---|
| lactose hydrous spray dried | 26.06 | 3.0 |
| anhydrous dibasic calcium phosphate | 73.85 | 8.50 |
| HPMC K4M | 26.06 | 3.0 |
| poloxamer 407 (micronized grade)[2] | 173.8 | 20.0 |
| sodium stearyl fumarate | 8.69 | 1.0 |
| magnesium stearate | 13.03 | 1.50 |

[1]Form 1 crystalline monopotassium salt of Compound A; conversion factor = 1.086.
[2]Obtained from BASF. Median particle size = 50 μm.

Compressed tablets containing 400 mg of Compound A on a free phenol basis were prepared by a roller compaction and tablet compression process train. Poloxamer 407, magnesium stearate, and sodium stearyl fumarate were pre-screened through No. 30 and No. 60 mesh size screens in succession, and then blended with all of the other ingredients, except for the extragranular magnesium stearate, in a Patterson-Kelly (PK) V-blender for 5 minutes. The blended material was then sieved through a No. 35 screen mesh to break up agglomerates, and the sieved material was then blended further in the same PK blender for about 15-20 minutes. The blend was then roller compacted using a Freund Type TF mini roller compactor at a roll pressure of 40 Kgf/cm$^2$, roll speed of 3 rpm and screw speed of 10 rpm. The resulting ribbon was milled in a small Quadro Comil fitted with a round impeller, screen size 39R (i.e., round hole size 0.039 inches; approximately mesh size No. 20) and operated at 1700 rpm. The resulting granules were then blended with 0.5% extragranular magnesium stearate in the PK blender for 5 minutes to produce the final blend. The lubricated granules were then compressed into tablets using a rotary tablet press with plain oval shaped tooling at a compression force necessary to achieve a tablet hardness of 16 to 20 kiloponds (i.e., 156.9 to 196.1 Newtons) as measured by using a Key model HT-300 hardness tester.

EXAMPLE 4

Preparation of Film-Coated Compressed Tablets Containing Compound a Potassium Salt Compressed tablets having the following composition were prepared in accordance with the procedure described in Example 5:

| Ingredient | Amount per Tablet (mg) | Amt per batch (wt. percent) |
|---|---|---|
| Compound A K salt[1] (on free phenol basis) | 434.4 (400) | 54.3 (50.0) |
| microcrystalline cellulose (AVICEL PH-102; extragranular) | 141.8 | 17.725 |
| dibasic calcium phosphate | 141.8 | 17.725 |
| croscarmellose sodium | 24.0 | 3.0 |
| HPMC 2910 (6 centipoise) | 40.0 | 5.0 |
| magnesium stearate (intragranular) | 8.0 | 1.0 |
| magnesium stearate (extragranular) | 10.0 | 1.25 |
| Opadry White 20 A 18273 (film coating) | 16.0[2] | 4.0[2] |

[1]Form 1 crystalline monopotassium salt of Compound A; conversion factor = 1.086.
[2]Target weight gain during film coating with respect to the core tablet.

EXAMPLE 5

Preparation of Film-Coated Compressed Tablets Containing Compound a Potassium Salt

| Ingredient | Amount per Tablet (mg) | Amt per batch (wt. percent) |
|---|---|---|
| Compound A K salt[1] (on free phenol basis) | 434.4 (400) | 54.3 (50.0) |
| microcrystalline cellulose (AVICEL PH-102; extragranular) | 187.7 | 23.5 |
| lactose monohydrate | 93.9 | 11.7 |
| croscarmellose sodium | 24.0 | 3.0 |
| HPMC 2910 (6 centipoise) | 40.0 | 5.0 |
| magnesium stearate (intragranular) | 6.0 | 0.75 |
| magnesium stearate (extragranular) | 14.0 | 1.75 |
| Opadry White 20 A 18273 (film coating) | 16.0[2] | 4.0[2] |

[1]Form 1 crystalline monopotassium salt of Compound A; conversion factor = 1.086.
[2]Target weight gain during film coating with respect to the core tablet.

Compressed tablets containing 400 mg of Compound A on a free phenol basis were prepared by blending all of the ingredients listed above, except for the extragranular microcrystalline cellulose, magnesium stearate and Opadry White, in a blender (Patterson-Kelly V blender; hereinafter the "V-blender") for 10 minutes, followed by lubrication for 5 minutes with intragranular magnesium stearate in the same blender. The blend was then roller compacted into ribbons in an Alexanderwerk WP 120 roller compactor using a 25 mm knurled roll at 60 bar roll pressure. The ribbons were subsequently milled into granules using the rotary fine granulator (an integral part of the WP 120 roller compactor) equipped with 2.0 mm and 0.8 mm size screens. The granules were then blended with extragranular microcrystalline cellulose in the V-blender for 10 minutes, followed by 5 minutes lubrication with the extragranular magnesium stearate in the same blender. The lubricated granules were then compressed on a rotary tablet press (Korsch) to 800 mg image tablets using 2×$^{16}$/$_{32}$" standard round concave tooling. The hardness of the core tablets was measured to be between 10 to 15 kiloponds (kp=1 kgf). The core tablets were then coated with Opadry White in a Vector film coater (1.3 L pan) to afford film-coated tablets with approximately a 4% weight gain with respect to the core tablet.

EXAMPLE 6

Preparation of Compressed Tablets Containing Compound a Potassium Salt

Part A—

| Ingredient | Amount per Tablet (mg) | Amt per batch (wt. percent) |
|---|---|---|
| Compound A K salt[1] (on free phenol basis) | 111.2 (100) | 27.8 (25.0) |
| microcrystalline cellulose (AVICEL PH-102) | 189.6 | 47.4 |
| lactose monohydrate | 63.2 | 15.8 |
| croscarmellose sodium | 12.0 | 3.0 |
| HPMC 2910 (6 centipoise) | 20.0 | 5.0 |

-continued

| Ingredient | Amount per Tablet (mg) | Amt per batch (wt. percent) |
|---|---|---|
| magnesium stearate (intragranular) | 2.0 | 0.5 |
| magnesium stearate (extragranular) | 2.0 | 0.5 |

[1]Form 1 crystalline monopotassium salt of Compound A; conversion factor (including purity) = 1.112.

Compressed tablets containing 100 mg of Compound A on a free phenol basis were prepared by blending all of the ingredients listed above, except for the extragranular magnesium stearate, in a blender (Turbula® Type T2F shaker-mixer, Basel, Switzerland) for 10 minutes. Portions of the blended material weighing approximately 1 gram were compressed into compacts (or slugs) in a benchtop press (Auto Carver Model Auto "C", Catalog No. 3888, Carver, Inc., Wabash, Ind.) using 1×0.5 inch rectangular tooling to 12 MPa (4 KN). The slugs were then sized into granules by passing them through a sieve with 1 mm openings. The granules were blended with the extragranular magnesium stearate in the Turbula blender for 5 minutes, and the lubricated granules were compressed into tablets using the Auto Carver press with 13/32-inch standard concave round tooling.

Part B—

| Ingredient | Amount per Tablet (mg) | Amt per batch (wt. percent) |
|---|---|---|
| Compound A K salt[1] (on free phenol basis) | 110 (100) | 27.5 (25.0) |
| microcrystalline cellulose (AVICEL PH-102) | 175.2 | 43.8 |
| microcrystalline cellulose (AVICEL PH-105) | 9.2 | 2.3 |
| lactose monohydrate | 61.6 | 15.4 |
| croscarmellose sodium | 12.0 | 3.0 |
| HPMC 2910 (6 centipoise) | 20.0 | 5.0 |
| magnesium stearate (intragranular) | 4.0 | 1.0 |
| magnesium stearate (extragranular) | 8.0 | 2.0 |

[1]Form 1 crystalline monopotassium salt of Compound A; conversion factor (including purity) = 1.112.

Compressed tablets having the composition set forth in the above table were prepared using a procedure similar to that set forth in Part A.

EXAMPLE 7

Pharmacokinetic Study in Healthy Human Males

An open-label, 4-period, partially randomized, crossover study investigating the pharmacokinetics of single oral doses of formulations containing the potassium salt of Compound A was conducted in healthy human males in the fasted state. Each subject received in succession a single dose of:

(A) a compressed tablet containing 400 mg of Compound A (free phenol basis) and having a composition and manner of preparation similar to that set forth in Example 3, (B) a compressed tablet containing 400 mg of Compound A (free phenol basis) and having a composition and manner of preparation similar to that set forth in Example 4, (C) a compressed tablet containing 400 mg of Compound A (free phenol basis) and having a composition and manner of preparation similar to that set forth in Example 5, and (D) four compressed tablets each containing 100 mg of Compound A (free phenol basis) and having a composition and manner of preparation similar to that set forth in Part B of Example 6.

Blood samples were taken predose and at 0.5, 1, 1.5, 2, 3, 4, 5, 6, 8, 10, 12, 16, 24, 32, 48 and 72 hours postdose. There was at least a 4-day washout period between each of doses A, B, C and D starting from the dose administration of the previous period. The safety of the subjects was monitored prior and subsequent to each dosing by clinical evaluation of adverse experiences and by inspection of other safety parameters including blood and urine laboratory safety tests, vital signs, physical examinations, and electrocardiograms.

Sample preparation and analysis: The plasma samples were extracted using 96-well liquid-liquid extraction. Plasma extracts were injected onto an Ace $C_{18}$ (50×3.0 mm, 3 µm, titanium rits) HPLC column and analyzed under isocratic conditions with a mobile phase consisting of 42.5/57.5 (v/v %) 0.1 mM EDTA in 0.1% formic acid/methanol, at a flow rate of 0.5 mL/minute. The sample extracts were ionized using an APCI interface and were monitored by MRM in the positive ionization mode. The dynamic range of the LC/MS/MS assay was 2-1000 ng/1 mL based on a 200 µL aliquot of human plasma.

PK Calculations: Area under the curve for a plot of plasma concentration v. time to last detectable concentration ($AUC_{0-last}$), was calculated using a non-compartmental model and the Linear Up/Log Down calculation method in WinNonLin Version 4.1. Data points after $C_{max}$ were fitted to a biexponential equation ($A^*\exp(-\alpha t)+B^*\exp(-\beta t)$) using WinNonlin v4.1, and AUC values were extrapolated to infinity according to the following equation: $AUC_{0-\infty}=AUC_{0-last}+C_{last}/\beta$, where $C_{last}$ is the last detectable concentration and $\beta$ comes from the above-noted biexponential equation. Observed maximum plasma concentration ($C_{max}$), time of $C_{max}$ ($T_{max}$), and plasma concentration at 12 hr post dosing ($C_{12hr}$) were determined by inspection.

The results of the study were as follows:

1. The dose A tablets afforded on average a $C_{max}$ that was about 58% lower and a $T_{max}$ that was about 2 hours longer than the corresponding values obtained for the dose D tablets. There was no change in the average $C_{12hr}$ for the dose A tablets compared to the dose D tablets, and the average $AUC_{0-\infty}$ for the dose A tablets was about 40% lower than the dose D tablets.

2. The dose A tablets afforded on average a $C_{max}$ that was about the same and a $T_{max}$ that was about 1 hour longer than the corresponding values obtained for the dose B tablets. There was an approximately 20% increase in the average $C_{12hr}$ for the dose A tablets compared to the dose B tablets, and the average $AUC_{0-\infty}$ for the dose A tablets was about 14% higher than for the dose B tablets.

3. The dose A tablets afforded on average a $C_{max}$ that was about 45% lower and a $T_{max}$ that was about 1.5 hours longer than the corresponding values obtained for the dose C tablets. There was an approximately 20% increase in the average $C_{12hr}$ for the dose A tablets compared to the dose C tablets, and the average $AUC_{0-\infty}$ for the dose A tablets was about 20% lower than that for the dose C tablets.

Compared to the dose C and D tablets [lactose-based comparator formulations with 25 wt. % (100 mg Compound A/tablet) and 50 wt. % (400 mg Compound A/tablet) drug loading on a free phenol basis, respectively], dose A tablets

[poloxamer-based formulation of the present invention with 46 wt. % (400 mg Compound A/tablet) drug loading on a free phenol basis] resulted in a lower $C_{max}$ and increased $T_{max}$. These characteristics may result in improved tolerability with chronic dosing, were any $C_{max}$-related toxicities to appear. Compared to the lactose formulation with the same drug loading (dose C), dose A also resulted in somewhat higher $C_{12hr}$ levels. Trough concentrations (e.g., for twice-daily dosing regimens) may therefore be modestly improved by dose A, a potential advantage for efficacy. A possible disadvantage of dose A tablets is their lower bioavailability compared to the dose C and dose D tablets, but trough concentrations are believed to be more relevant for efficacy, and the shape of the plasma concentration profile for dose A (lower $C_{max}$, same or higher $C_{12hr}$) is believed to be more favorable for balancing tolerability and efficacy compared to dose C and dose D. Compared to dose B [calcium phosphate-based comparator formulation with 50 wt. % (400 mg Compound A/tablet) drug loading on a free phenol basis], dose A had the advantage of increased $T_{max}$, somewhat increased $C_{12hr}$ values and somewhat higher bioavailability.

EXAMPLE 8

In Vitro Dissolution Studies

Figure 3:
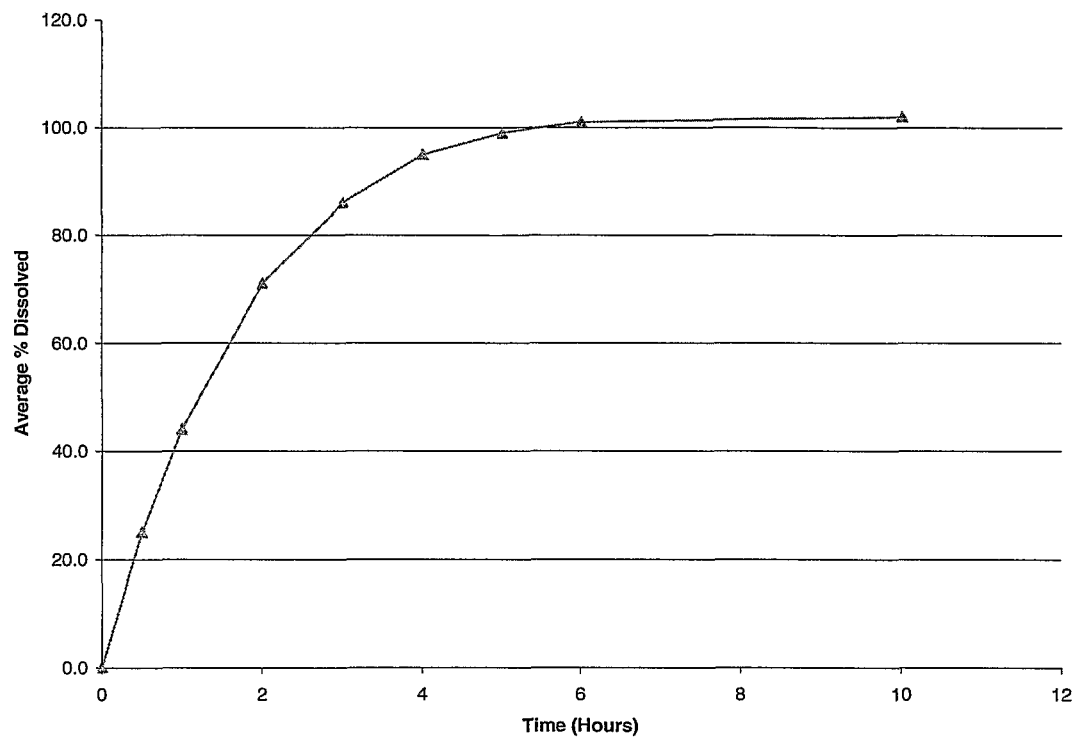
FIG. 3 is a plot of dissolution data from the dissolution studies described in Example 8; i.e., a plot of the percent of Compound A dissolved versus dissolution time for the dissolution study of poloxamer-containing tablets with 400 mg of Compound A.

The dissolution properties of tablets prepared in the manner described in Example 3 (i.e., poloxamer-containing tablets with 400 mg of Compound A on a free phenol basis) were tested in the following manner: A single tablet was added to a USP Type II dissolution vessel containing 900 mL of 0.025 M sodium phosphate buffer (pH=6.8) as the dissolution medium. The temperature of the medium was controlled at 37° C. After the basket style sinker containing one tablet was allowed to sink to the bottom of the vessel, the medium was stirred at 100 rpm for 10 hours. Samples (1.0 mL) were removed from the medium at 0.5, 1, 2, 3, 4, 5, 6, 8 and 10 hours. Each sample was then analyzed via HPLC to determine the concentration of Compound A in the solution. The potassium salt of Compound A was employed as the reference standard, so a conversion factor of 0.9211 was used to obtain the results in terms of the free phenol form. The dissolution properties of five additional tablets were subsequently determined using this procedure. FIG. 3 presents the results as a plot of the average percent of Compound A dissolved versus dissolution time.

HPLC: column=Merck KGaA Chromolith Performance RP-18e (100×4.6 mm); mobile phase=38:62 (v:v) of ACN: 0.01M K phosphate (pH=3.0); flow rate=5.0 mL/minute; column temperature=40° C.; injection volume=10 μL; detection wavelength=303 nm; run time=1 minute.

Figure 4:
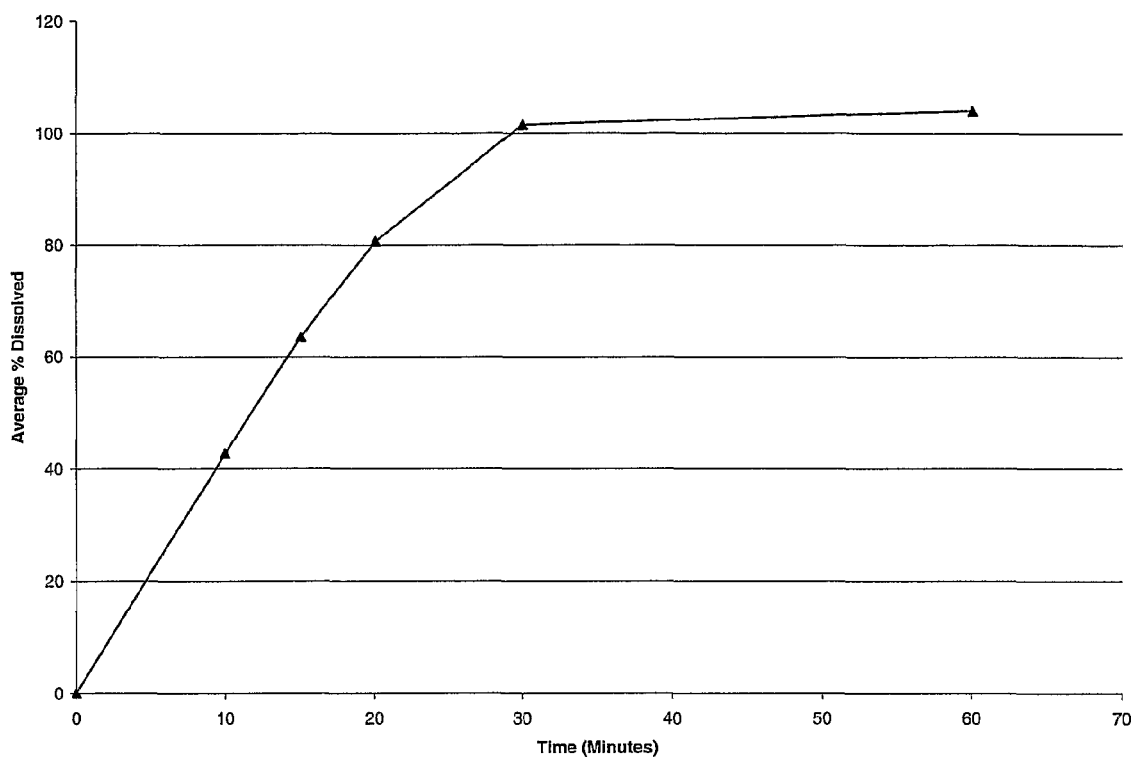
FIG. 4 is a plot of dissolution data from the dissolution studies described in Example 8; i.e., a plot of the percent of Compound A dissolved versus dissolution time for the dissolution study of lactose-containing tablets with 100 mg of Compound A.

The dissolution properties of the tablets prepared in the manner described in Part B of Example 6 (i.e., lactose-containing tablets with 100 mg of Compound A on a free phenol basis) were determined in the following manner: A single tablet was added to a USP Type II dissolution vessel containing 900 mL of 0.025 M sodium phosphate buffer (pH=6.8)/0.5% SDS as the dissolution medium. The temperature of the medium was controlled at 37° C. After one tablet was allowed to sink to the bottom of the vessel, the medium was stirred at 75 rpm for 60 minutes. Samples (5.0 mL) were removed from the medium at 10, 15, 20, 30 and 60 minutes. Each sample was then analyzed via HPLC to determine the concentration of Compound A in the solution. The potassium salt of Compound A was employed as the reference standard, so a conversion factor of 0.9211 was used to obtain the results in terms of the free phenol form. The dissolution properties of five additional tablets were subsequently determined using this procedure. FIG. 4 represents the results as a plot of the percent of Compound A dissolved versus dissolution time.

HPLC: column=Waters Atlantis $dC_{18}$ (150×4.6 mm, 5 μm); mobile phase=45:55 (v:v) of ACN: 0.01M K phosphate (pH=3.0); flow rate=1.5 mL/minute; column temperature=40° C.; injection volume=40 μL; detection wavelength=303 nm; run time=5 minutes.

The dissolution properties of the tablets prepared in the manner described in Example 5 (i.e., lactose-containing tablets with 400 mg of Compound A on a free phenol basis) were determined in the same manner as for the Example 6 tablets, except that the pH 6.8 buffered media did not contain SDS (which can assist dissolution), the paddle rotation speed was at 100 RPM, and only 1.0 mL samples of the dissolution media were removed at the timepoints. Two tablets were tested and analyzed by HPLC with the method using the Chromolith Column.

The dissolution profile for the tablets of Example 3 showed a slower rate of drug release as compared with the tablets of Example 6. More particularly, for the Example 3 tablets, the average time for attaining 80% dissolution of Compound A was between 2 and 3 hours, whereas for the average time for 80% dissolution of Compound A for the Example 6 tablets was about 20 minutes. The Example 5 tablets exhibited a quick dissolution profile (i.e., 80+% dissolution in less than 20 minutes), similar to that of the Example 6 tablets, even though SDS was not present in the media.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A pharmaceutical formulation for oral administration as a solid dose, which comprises an effective amount of a potassium salt of Compound A and a release rate controlling composition comprising a solubilizing agent, a gelling agent, and optionally a water soluble filler, wherein Compound A is:

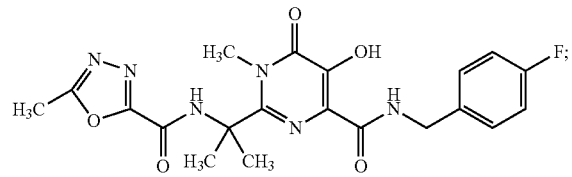 [SMILES: Cc1nnc(C(=O)NC(C)(C)c2nc(C(=O)NCc3ccc(F)cc3)c(O)c(=O)n2C)o1]

the solubilizing agent comprises a poloxamer, the gelling agent comprises a high-viscosity hydroxypropylmethylcellulose; and the optional water soluble filler comprises lactose, and wherein:
 the potassium salt of Compound A is employed in an amount in a range of from about 25 to about 75 wt. % on a free phenol basis;
 the poloxamer is employed in an amount in a range of from about 10 to about 20 wt. %;
 the high-viscosity hydroxypropylmethylcellulose is employed in an amount in a range of from about 3 to about 9 wt. %; and
 the lactose is employed in an amount in a range of from 3 to about 9 wt. %.

2. The formulation according to claim 1, wherein the potassium salt of Compound A is the form 1 crystalline potassium salt of Compound A.

3. The formulation according to claim 1, wherein the poloxamer is poloxamer 407 milled to an average particle size in a range of from about 50 to about 150 microns; the high-viscosity hydroxypropylmethylcellulose is that produces a 2 wt. % aqueous solution having a viscosity of at least about 2900 centipoise (cps) at 20° C.; and the lactose is lactose hydrous spray dried.

4. The formulation according to claim 3, wherein the potassium salt of Compound A is Form 1 crystalline potassium salt of Compound A.

5. The formulation according to claim 1, which further comprises a diluent and a lubricant, wherein the diluent comprises microcrystalline cellulose and optionally calcium phosphate; and the lubricant comprises a metal stearate and a metal stearyl fumarate.

6. The formulation according to claim 5, wherein:
the potassium salt of Compound A is employed in an amount in a range of from about 40 to about 60 wt. % on a free phenol basis;
the microcrystalline cellulose is employed in an amount in a range of from about 5 to about 30 wt. %;
the calcium phosphate is employed in an amount in a range of from about zero to about 15 wt. %; and
the metal stearate and metal stearyl fumarate are each independently employed in an amount in a range of from about 1 to about 3 wt. %.

7. The formulation according to claim 6, wherein the potassium salt of Compound A is Form 1 crystalline potassium salt of Compound A; the poloxamer is poloxamer 407 milled to an average particle size in a range of from about 50 to 150 microns; the high-viscosity hydroxypropylmethylcellulose is HPMC having a viscosity of about 4000 mPa·sec that produces a 2 wt. % aqueous solution having a viscosity of at least about 2900 centipoise (cps) at 20° C.; the lactose is lactose hydrous spray dried; the microcrystalline cellulose has a nominal particle size of 100 µm, a bulk density of 0.28 to 0.33 g/cc and a moisture content of 3% to 5%; the calcium phosphate is dibasic calcium phosphate; the metal stearate is magnesium stearate; and the metal stearyl fumarate is sodium stearyl fumarate.

8. The formulation according to claim 1, wherein the potassium salt of Compound A is employed on a free phenol basis in an amount in a range of from about 100 mg to about 600 mg.

9. The formulation according to claim 8, wherein the formulation is encapsulated or compressed into a tablet.

10. The formulation according to claim 2, wherein the potassium salt of Compound A is employed on a free phenol basis in an amount in a range of from about 100 mg to about 600 mg.

11. A process for preparing a compressed tablet of a pharmaceutical formulation according to claim 5, wherein the method comprises:
(A) blending a mixture of the Compound A K salt, the solubilizing agent comprising the poloxamer, the gelling agent comprising the high-viscosity hydroxypropylmethylcellulose, the water-soluble filler comprising the lactose, the first diluent comprising the microcrystalline cellulose and calcium phosphate, a first portion of the first lubricant comprising part of the metal stearate and the metal stearyl fumarate;
(B) sieving the blended mixture, and then further blending the sieved mixture;
(C) rolling the sieved and blended mixture to form a compact, and then sizing the resulting compact to form granules;
(D) blending the granules with the remaining portion of the lubricant comprising the rest of the metal stearate; and
(E) compressing the lubricated granules of Step D to obtain the tablet.

12. The process according to claim 11, wherein:
the potassium salt of Compound A is employed in an amount in a range of from about 40 to about 60 wt. % on a free phenol basis;
the poloxamer is employed in an amount in a range of from about 10 to about 20 wt. %;
the high-viscosity hydroxypropylmethylcellulose is employed in an amount in a range of from about 3 to about 9 wt. %;
the lactose is employed in an amount in a range of from 3 to about 9 wt. %;
the microcrystalline cellulose and calcium phosphate are each independently employed in an amount in a range of from about 5 to about 25 wt. %; and
the metal stearate and metal stearyl fumarate are each independently employed in an amount in a range of from about 1 to about 3 wt. %.

13. The process according to claim 12, wherein the poloxamer is poloxamer 407 milled to an average particle size in a range of from about 50 to 150 microns; the high-viscosity hydroxypropylmethylcellulose having a viscosity of about 4000 mPa·sec that produces a 2 wt. % aqueous solution having a viscosity of at least 2900 centipoise at 20° C.; the lactose is lactose hydrous spray dried; the microcrystalline cellulose has a nominal particle size of 100 µm, a bulk density of 0.28 to 0.33 g/cc and a moisture content of 3% to 5%; the calcium phosphate is dibasic calcium phosphate; the metal stearate is magnesium stearate; and the metal stearyl fumarate is sodium stearyl fumarate.

14. The process according to claim 13, wherein the potassium salt of Compound A is Form 1 crystalline potassium salt of Compound A.

15. The process according to claim 12, wherein the process further comprises: (F) coating the compressed tablet with Opadry II HP to afford a coated tablet in which the coating is from about 2 to about 4% of the weight of the compressed tablet.

16. A method for the treatment of HIV infection in a subject in need thereof which comprises administering to the subject the pharmaceutical formulation according to claim 1.

* * * * *